(12) United States Patent
Quinn et al.

(10) Patent No.: US 12,070,331 B2
(45) Date of Patent: Aug. 27, 2024

(54) WEARABLE PHYSIOLOGICAL DEVICE AND APPARATUS

(71) Applicant: Nitto Denko Corporation, Osaka (JP)

(72) Inventors: Alan Quinn, Melbourne (AU); Colin Gehrig, Melbourne (AU); Denis Greco, Melbourne (AU); Marco Sebastiani, Melbourne (AU)

(73) Assignee: Nitto Denko Corporation (JP)

( * ) Notice: Subject to any disclaimer, the term of this patent is extended or adjusted under 35 U.S.C. 154(b) by 1031 days.

(21) Appl. No.: 16/977,361

(22) PCT Filed: Feb. 28, 2019

(86) PCT No.: PCT/SG2019/050112
§ 371 (c)(1),
(2) Date: Sep. 1, 2020

(87) PCT Pub. No.: WO2019/168475
PCT Pub. Date: Sep. 6, 2019

(65) Prior Publication Data
US 2021/0106278 A1    Apr. 15, 2021

(30) Foreign Application Priority Data
Mar. 2, 2018  (SG) .......................... 10201801744T

(51) Int. Cl.
*A61B 5/00*  (2006.01)
*A61B 5/01*  (2006.01)
*A61B 5/024*  (2006.01)

(52) U.S. Cl.
CPC ................ *A61B 5/681* (2013.01); *A61B 5/01* (2013.01); *A61B 5/02416* (2013.01);
(Continued)

(58) Field of Classification Search
CPC ....... A61B 5/681; A61B 5/01; A61B 5/02416; A61B 5/02438; A61B 5/7445;
(Continued)

(56) References Cited

U.S. PATENT DOCUMENTS 7,618,260 B2   11/2009  Daniel et al.
8,613,544 B2 * 12/2013  Kitahara ................ B29C 70/70
                                                          368/282
(Continued)

FOREIGN PATENT DOCUMENTS

EP      3009069 A2      4/2016
WO    2011094876 A1    8/2011
(Continued)

OTHER PUBLICATIONS

International Search Report for Application No. PCT/SG2019/050112 mailed May 23, 2019, 3 pages.
(Continued)

*Primary Examiner* — Sean D Mattson
(74) *Attorney, Agent, or Firm* — Lerner David LLP

(57) ABSTRACT

An aspect of the present disclosure generally relates to a wearable physiological device comprising: (a) a first housing assembly comprising: a first housing body; a first circuit assembly removably coupled to the first housing body; a user interface assembly communicatively connected to the first circuit assembly; and (b) a second housing assembly removably coupled to the first housing assembly, the second housing assembly comprising: a second housing body; a second circuit assembly removably coupled to the second housing body, the second circuit assembly comprising a set of physiological sensors; a removable battery disposed on the second circuit assembly; and a flexible connector communicatively connecting the second circuit assembly to the first circuit assembly, wherein the set of physiological sen-
(Continued)

sors are configured for measuring physiological signals from a user wearing the wearable physiological device, the physiological signals communicable to the user interface assembly.

20 Claims, 22 Drawing Sheets

(52) U.S. Cl.
CPC ........ *A61B 5/02438* (2013.01); *A61B 5/7445* (2013.01); *A61B 2560/0214* (2013.01); *A61B 2560/0443* (2013.01); *A61B 2562/18* (2013.01); *A61B 2562/222* (2013.01); *A61B 2562/227* (2013.01)

(58) Field of Classification Search
CPC .... A61B 2560/0214; A61B 2560/0443; A61B 2562/18; A61B 2562/222; A61B 2562/227; G04G 21/025; G06F 1/163; G06F 1/16
See application file for complete search history.

(56) References Cited

U.S. PATENT DOCUMENTS

| | | | |
|---|---|---|---|
| 9,685,802 B1* | 6/2017 | Mirov | .................... H02J 7/0044 |
| 9,711,060 B1 | 7/2017 | Lusted et al. | |
| 2011/0221688 A1* | 9/2011 | Byun | ..................... H04B 1/385 |
| | | | 345/173 |
| 2014/0107493 A1* | 4/2014 | Yuen | .................... A61B 5/7455 |
| | | | 600/479 |
| 2014/0180019 A1* | 6/2014 | Martinez | ................ A61B 5/681 |
| | | | 600/300 |
| 2014/0247137 A1* | 9/2014 | Proud | .................... G16H 40/63 |
| | | | 320/108 |
| 2015/0105221 A1* | 4/2015 | Roush | .................... G16H 20/30 |
| | | | 482/8 |
| 2015/0265214 A1 | 9/2015 | De Kok et al. | |
| 2015/0340891 A1* | 11/2015 | Fish | ....................... H02J 7/342 |
| | | | 320/103 |
| 2018/0220972 A1* | 8/2018 | Jeong | ................... A61B 5/7445 |
| 2019/0388028 A1* | 12/2019 | Kim | ..................... H02J 50/005 |

FOREIGN PATENT DOCUMENTS

| | | |
|---|---|---|
| WO | 2015168590 A1 | 11/2015 |
| WO | 2017136383 A1 | 8/2017 |

OTHER PUBLICATIONS

Search Report for European Application No. 19760011 dated Oct. 29, 2021. 2 pgs.

* cited by examiner

WEARABLE PHYSIOLOGICAL DEVICE AND APPARATUS

CROSS REFERENCE TO RELATED APPLICATION(S)

The present disclosure claims the benefit of Singapore Patent Application No. 10201801744T filed on 2 Mar. 2018, which is incorporated in its entirety by reference herein.

TECHNICAL FIELD

The present disclosure generally relates to a wearable physiological device and apparatus. More particularly, the present disclosure describes various embodiments of a physiological device wearable on a user, e.g. on a wrist, for measuring physiological signals from the user, as well as a physiological apparatus including the wearable physiological device and a docking station for charging the wearable physiological device.

BACKGROUND

People are increasingly aware of consumer technologies and devices for home use and self-monitoring of their health. Particularly, there are various types of wearable devices which people can wear to obtain various data pertaining to their health. These wearable devices usually have various sensors to measure physiological signals such as heart rate and blood pressure. However, these wearable devices are often worn for long periods for data collection and passive health monitoring, and there is a tendency for the devices to break down or become damaged after prolonged usage. Users will need to replace the damaged devices, leading to increased expenses.

United States Patent Publications 20150296963 and 20150261189 describe some examples of wearable devices with sensors. Particularly, these devices have a head assembly that can be removed from the wrist straps. If the devices become damaged after prolonged usage, users may potentially replace only the head assemblies. However, the head assemblies have to be replaced in its entirety. With the head assemblies being likely the most expensive component of the device, replacement of the head assemblies will still result in increased expenses. There is thus a limited scope as to how users can replace/repair wearable devices or various components thereof.

Therefore, in order to address or alleviate at least one of the aforementioned problems and/or disadvantages, there is a need to provide a wearable physiological device and apparatus, in which there is at least one improvement and/or advantage over the prior art.

SUMMARY

According to a first aspect of the present disclosure, there is a wearable physiological device comprising: (a) a first housing assembly comprising: a first housing body; a first circuit assembly removably coupled to the first housing body; a user interface assembly communicatively connected to the first circuit assembly; and (b) a second housing assembly removably coupled to the first housing assembly, the second housing assembly comprising: a second housing body; a second circuit assembly removably coupled to the second housing body, the second circuit assembly comprising a set of physiological sensors; a removable battery disposed on the second circuit assembly; and a flexible connector communicatively connecting the second circuit assembly to the first circuit assembly, wherein the set of physiological sensors are configured for measuring physiological signals from a user wearing the wearable physiological device, the physiological signals communicable to the user interface assembly.

According to a second aspect of the present disclosure, there is a physiological apparatus comprising: (a) a wearable physiological device comprising: (i) a first housing assembly comprising: a first housing body; a first circuit assembly removably coupled to the first housing body; and a user interface assembly communicatively connected to the first circuit assembly; (ii) a second housing assembly removably coupled to the first housing assembly, the second housing assembly comprising: a second housing body; a second circuit assembly removably coupled to the second housing body, the second circuit assembly comprising a set of physiological sensors for measuring physiological signals; a removable battery disposed on the second circuit assembly; and a set of electrical contacts disposed on the second housing body; (b) a docking station for docking the wearable physiological device thereto in one orientation, the docking station comprising: (i) a docking assembly; and (ii) a set of electrical connectors disposed on the docking assembly, the electrical connectors aligned to the electrical contacts of the wearable physiological device upon said docking, wherein the electrical connectors are connectable to the electrical contacts upon said docking for charging the battery.

An advantage of one or more of the above aspects of the present disclosure is that the first housing assembly and second housing assembly, as well as various components thereof, are removably coupled together and thus can be disassembled and reassembled by the user. These components can be easily replaced by the user if they become damaged or are worn out after prolonged use. Advantageously, it will not be necessary for the user to replace the entire physiological device if only one or some components are damaged, thus reducing their expenditure on repairs. The user is given more control of the physiological device and this helps to extend the lifespan of the physiological device.

A wearable physiological device and apparatus according to the present disclosure are thus disclosed herein. Various features, aspects, and advantages of the present disclosure will become more apparent from the following detailed description of the embodiments of the present disclosure, by way of non-limiting examples only, along with the accompanying drawings.

DETAILED DESCRIPTION

Figure 1A:
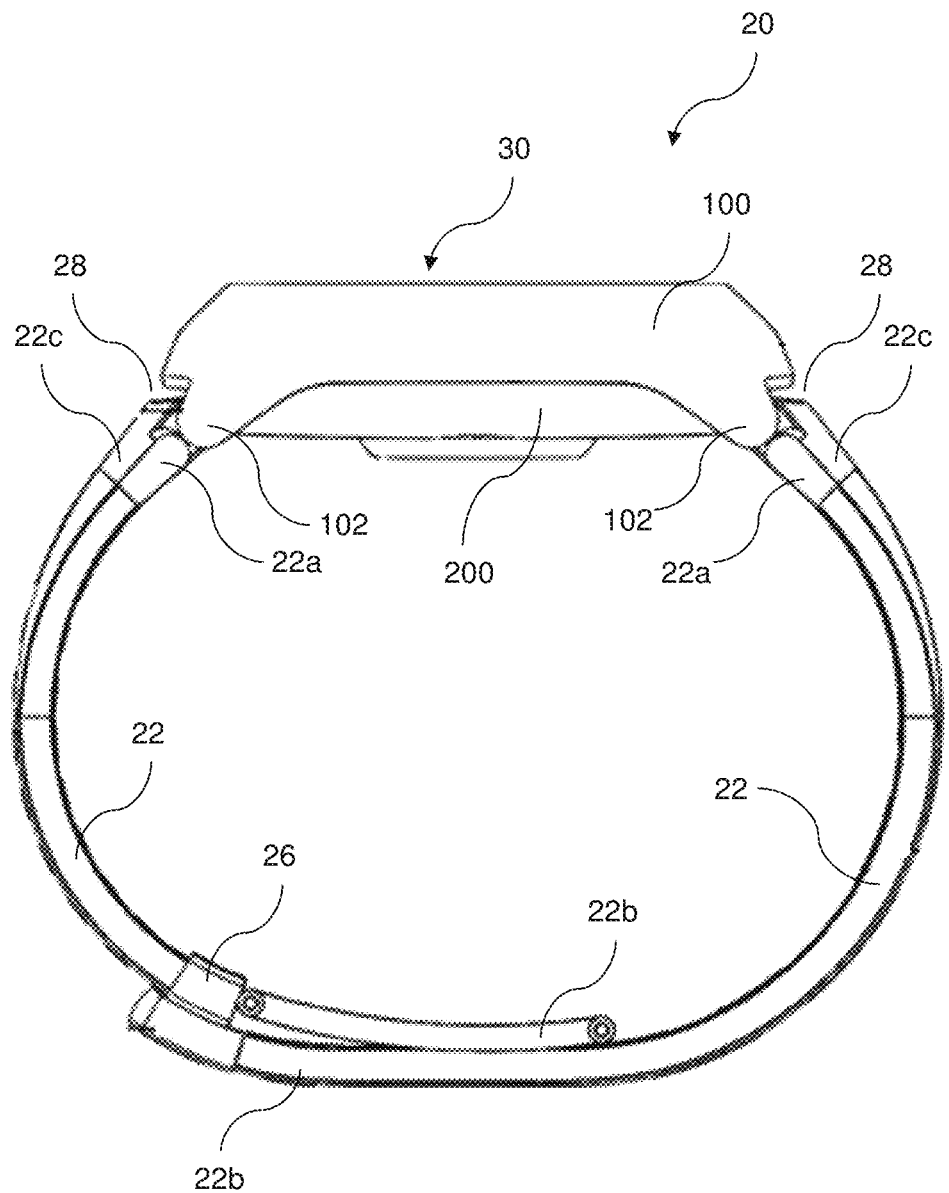
FIG. 1A to FIG. 1D illustrate various views of a wearable physiological device, in accordance with an embodiment of the present disclosure.

In the present disclosure, depiction of a given element or consideration or use of a particular element number in a particular figure or a reference thereto in corresponding descriptive material can encompass the same, an equivalent, or an analogous element or element number identified in another figure or descriptive material associated therewith. The use of "/" in a figure or associated text is understood to mean "and/or" unless otherwise indicated. As used herein, the term "set" corresponds to or is defined as a non-empty finite organization of elements that mathematically exhibits a cardinality of at least one (e.g. a set as defined herein can correspond to a unit, singlet, or single element set, or a multiple element set), in accordance with known mathematical definitions. The recitation of a particular numerical value or value range herein is understood to include or be a recitation of an approximate numerical value or value range.

For purposes of brevity and clarity, descriptions of embodiments of the present disclosure are directed to a wearable physiological device and a physiological apparatus, in accordance with the drawings. While aspects of the present disclosure will be described in conjunction with the embodiments provided herein, it will be understood that they are not intended to limit the present disclosure to these embodiments. On the contrary, the present disclosure is intended to cover alternatives, modifications and equivalents to the embodiments described herein, which are included within the scope of the present disclosure as defined by the appended claims. Furthermore, in the following detailed description, specific details are set forth in order to provide a thorough understanding of the present disclosure. However, it will be recognized by an individual having ordinary skill in the art, i.e. a skilled person, that the present disclosure may be practiced without specific details, and/or with multiple details arising from combinations of aspects of particular embodiments. In a number of instances, well-known systems, methods, procedures, and components have not been described in detail so as to not unnecessarily obscure aspects of the embodiments of the present disclosure.

References to "an embodiment/example", "another embodiment/example", "some embodiments/examples", "some other embodiments/examples", and so on, indicate that the embodiment(s)/example(s) so described may include a particular feature, structure, characteristic, property, element, or limitation, but that not every embodiment/example necessarily includes that particular feature, structure, characteristic, property, element or limitation. Furthermore, repeated use of the phrase "in an embodiment/example" or "in another embodiment/example" does not necessarily refer to the same embodiment/example. The terms "comprising", "including", "having", and the like do not exclude the presence of other features/elements/steps than those listed in an embodiment. Recitation of certain features/elements/steps in mutually different embodiments does not indicate that a combination of these features/elements/steps cannot be used in an embodiment. As used herein, the terms "a" and "an" are defined as one or more than one. The use of "/" in a figure or associated text is understood to mean "and/or" unless otherwise indicated.

As used herein, the terms "component", "module," "system", "interface", and the like are generally intended to refer to a computer-related entity, either hardware, a combination of hardware and software, software, or software in execution. For example, a component or a module may be, but is not limited to being, a process running on a processor, a processor, an object, an executable, a thread of execution, a program, and/or a computer. By way of illustration, both an application running on a controller and the controller can be a component/module. One or more components/modules may reside within a process and/or thread of execution.

Wearable Physiological Device

In representative or exemplary embodiments of the present disclosure, there is a wearable physiological device 20 as illustrated in FIG. 1A to FIG. 1D. Generally, the physiological device 20 is wearable on a user, e.g. worn on the wrist of the user, for monitoring of the user's physiological health and functions. The wearable physiological device 20 includes a head assembly 30 for performing various operations associated with said monitoring of the user's physiology. For example, the head assembly 30 is configured for collecting and processing physiological signals or data from the user. The processed data may provide the user with various types of information, such as relating to the user's activity, sleep or stress condition. Additionally, the head assembly 30 may be attachable to a separate retrieval platform where the user places a portion of the user's arm and/or fingers on the retrieval platform, further adding stability during monitoring of the user's physiological health.

The head assembly 30 includes a first housing assembly 100 and a second housing assembly 200 removably coupled to the first housing assembly 100. When worn on the user, the first housing assembly 100 is oriented above the second housing assembly 200, wherein the second housing assembly 200 faces towards a skin surface of the user.

The wearable physiological device 20 further includes a set of straps or bands 22 for strapping around or circumscribing the user's wrist. In some embodiments, there is a single continuous strap 22 and the head assembly 30 is removably attached or coupled to the strap 22, such as by attachment, e.g. clipping, latching, and/or snapping, to a centre portion of the strap 22. The single continuous strap 22 attached to the head assembly 30 is wrappable around a portion of the user's wrist.

In some embodiments, the head assembly 30 includes a set of lugs 102. In one embodiment, the first housing assembly 100 includes a pair of lugs 102 on each side thereof. In each pair of lugs 102, the lugs 102 are separated longitudinally away from each other, i.e. along the length of the user's arm. The wearable physiological device 20 includes two separate straps 22 removably attached to the lugs 102. Specifically, each strap 22 has a proximal end 22a and a distal end 22b, the proximal end 22a removably attached to the respective pairs of lugs 102. The two separate straps 22 may be of similar/different lengths/widths, which when combined, circumscribe or enclose the user's wrist.

Figure 1B:
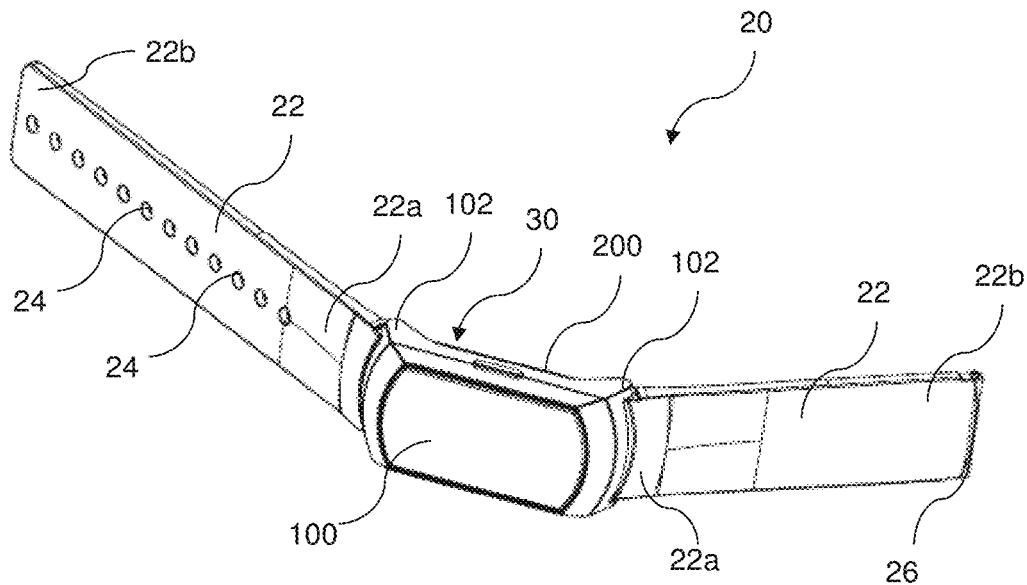
Figure 10:
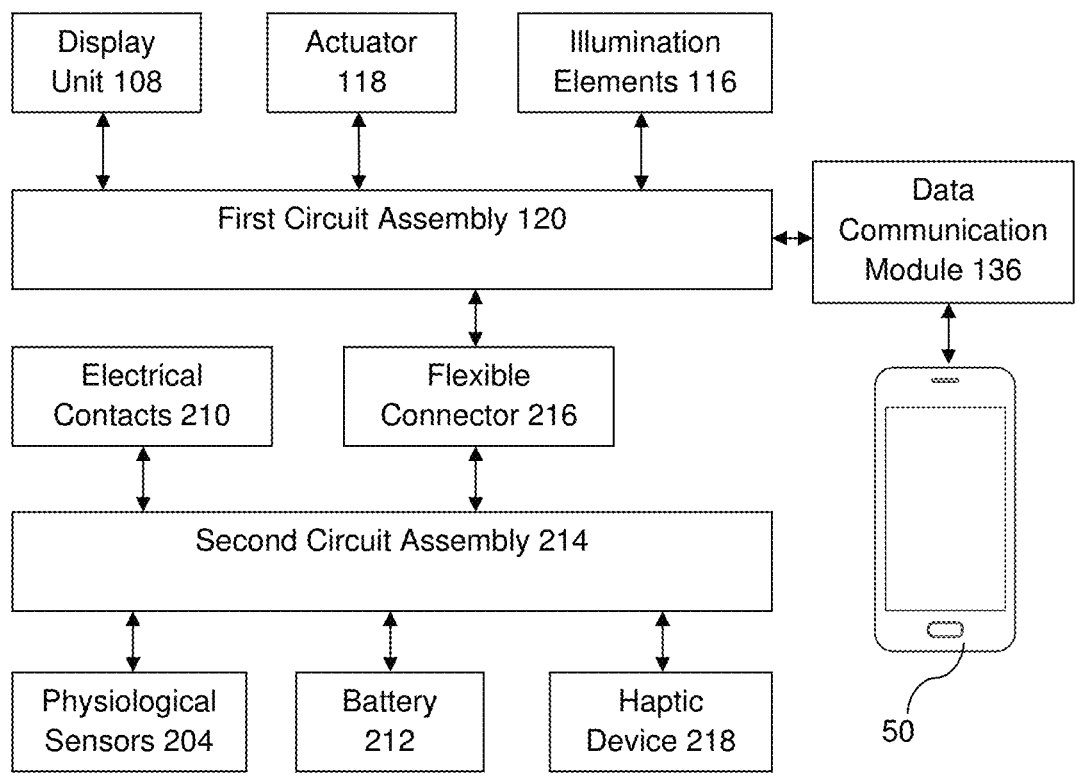
FIG. 10 illustrates a functional block diagram of the wearable physiological device, in accordance with an embodiment of the present disclosure.

In some embodiments as shown in FIG. 1B and FIG. 10, one of the straps 22 includes a plurality of holes or recessed portions 24. The other of the straps 22 includes a strap fastener 26 at the distal end 22b thereof. The strap fastener 26, such as or including a protrusion or hook element, is engageable with one of the holes 24 for wearing and adapting of the physiological device 20 on the user's wrist. The plurality of holes 24 provides the user with flexibility of fitting the physiological device 20 with various wrist sizes of the user. It will be appreciated that the strap fastener 26 can be in various forms known to the skilled person.

Figure 1C:
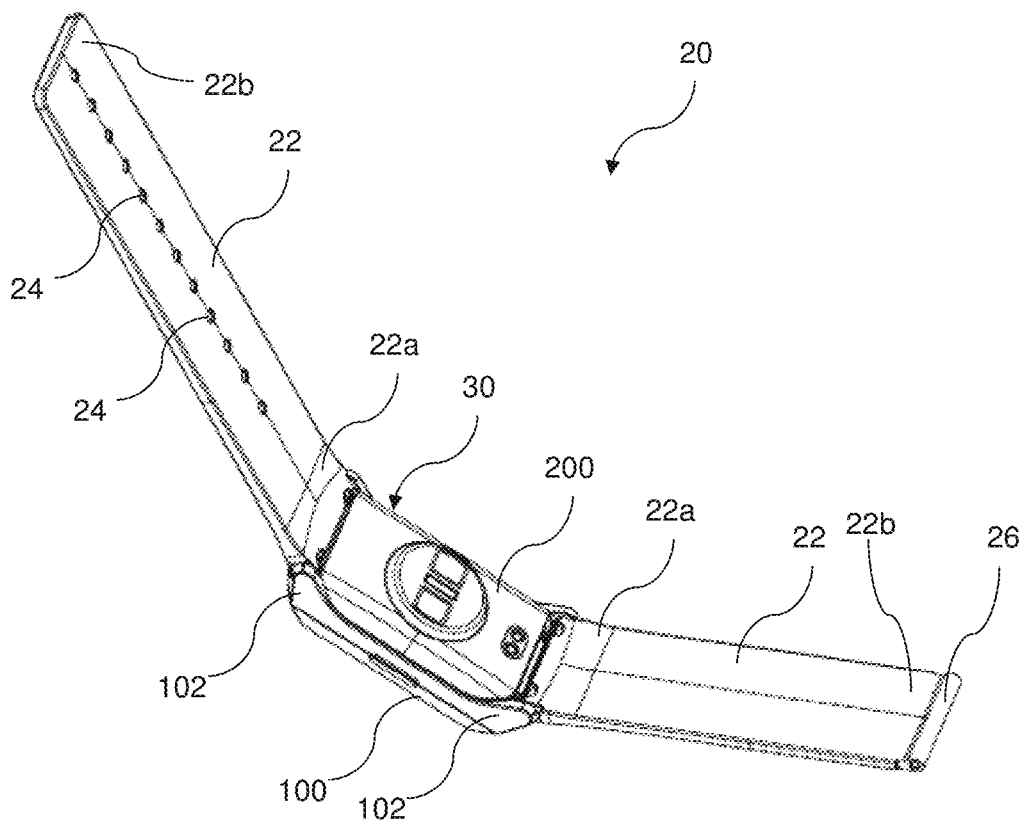
Figure 1D:
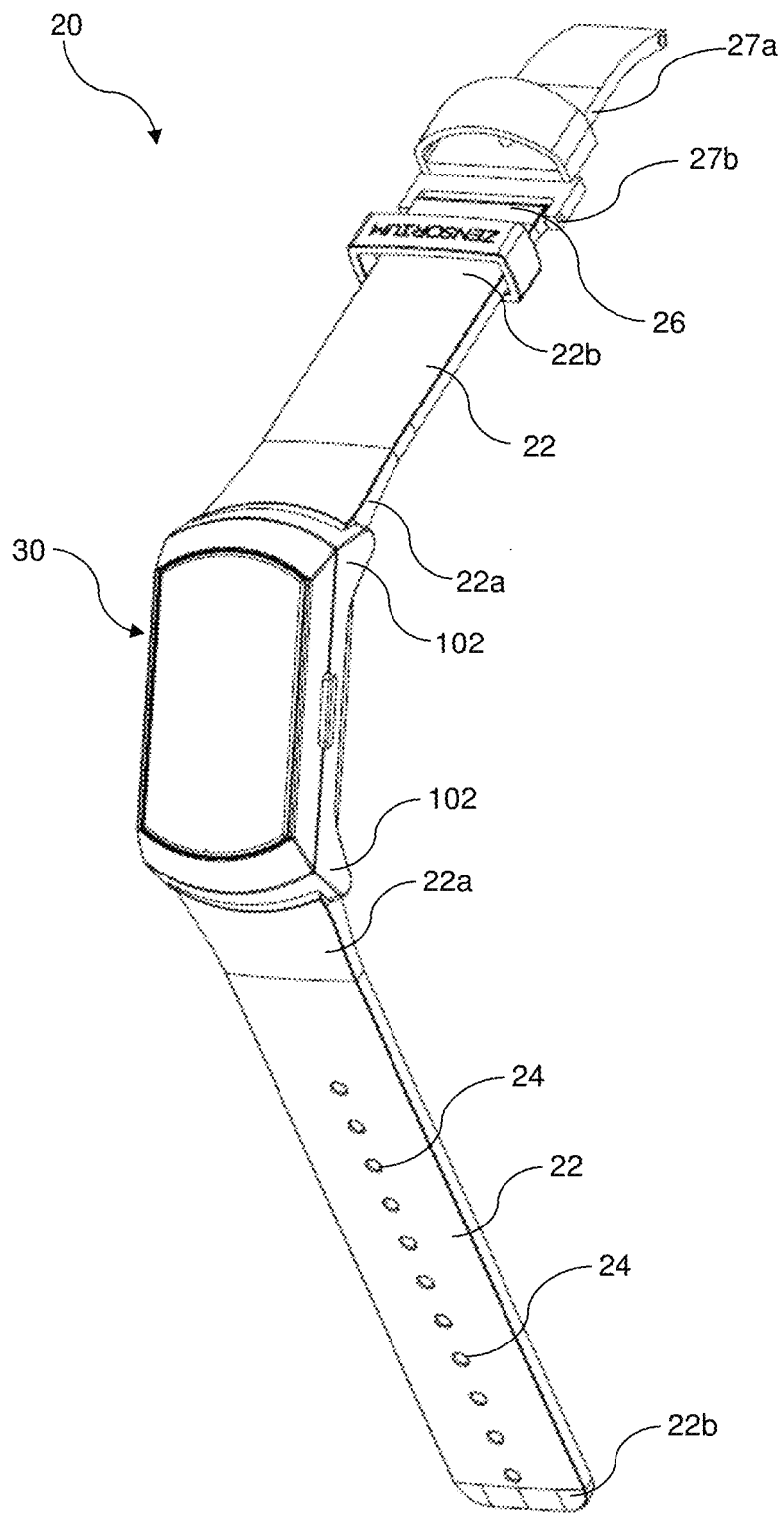
Figure 2A:
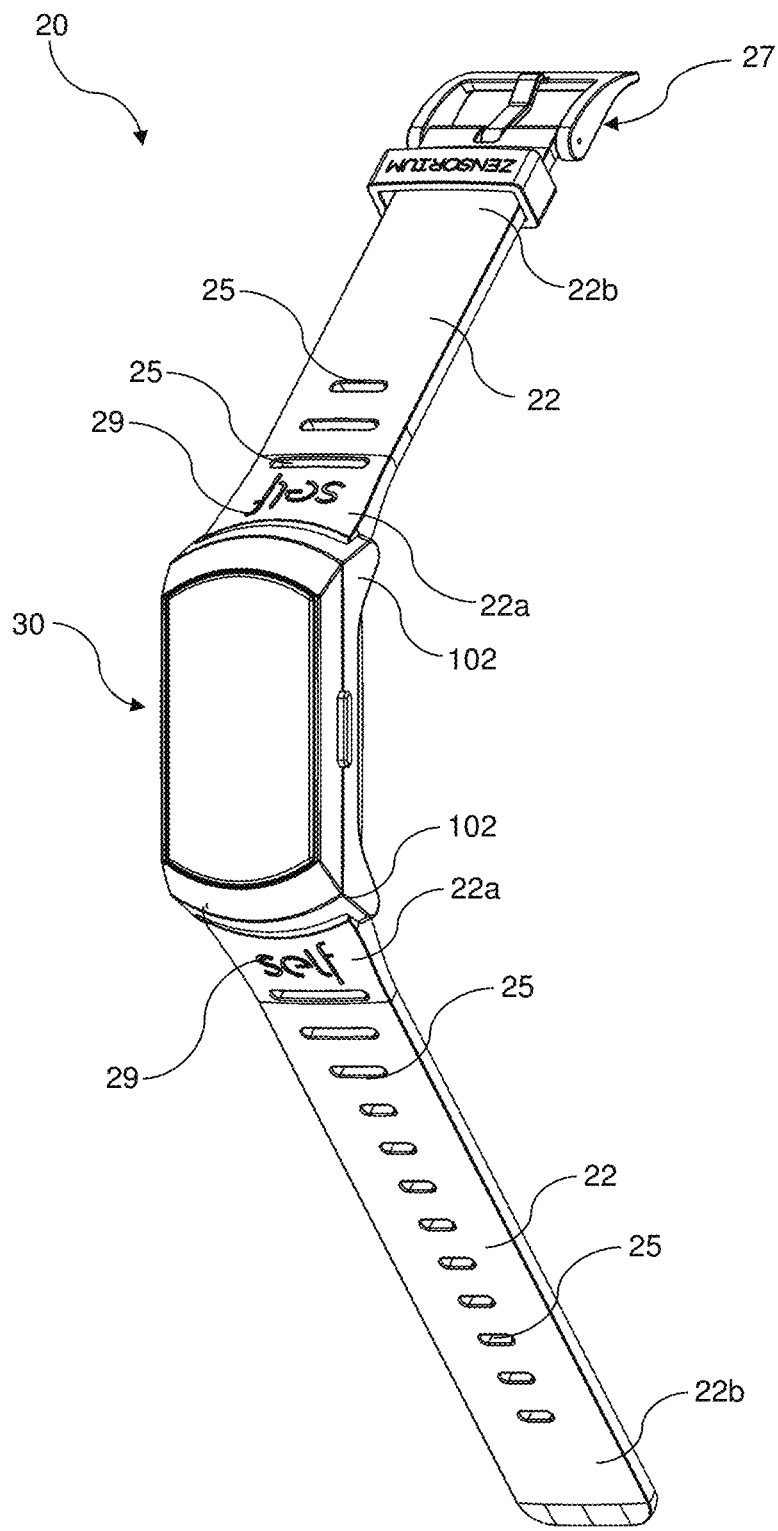
FIG. 2A and FIG. 2B illustrate various views of the wearable physiological device, in accordance with another embodiment of the present disclosure.
Figure 2B:
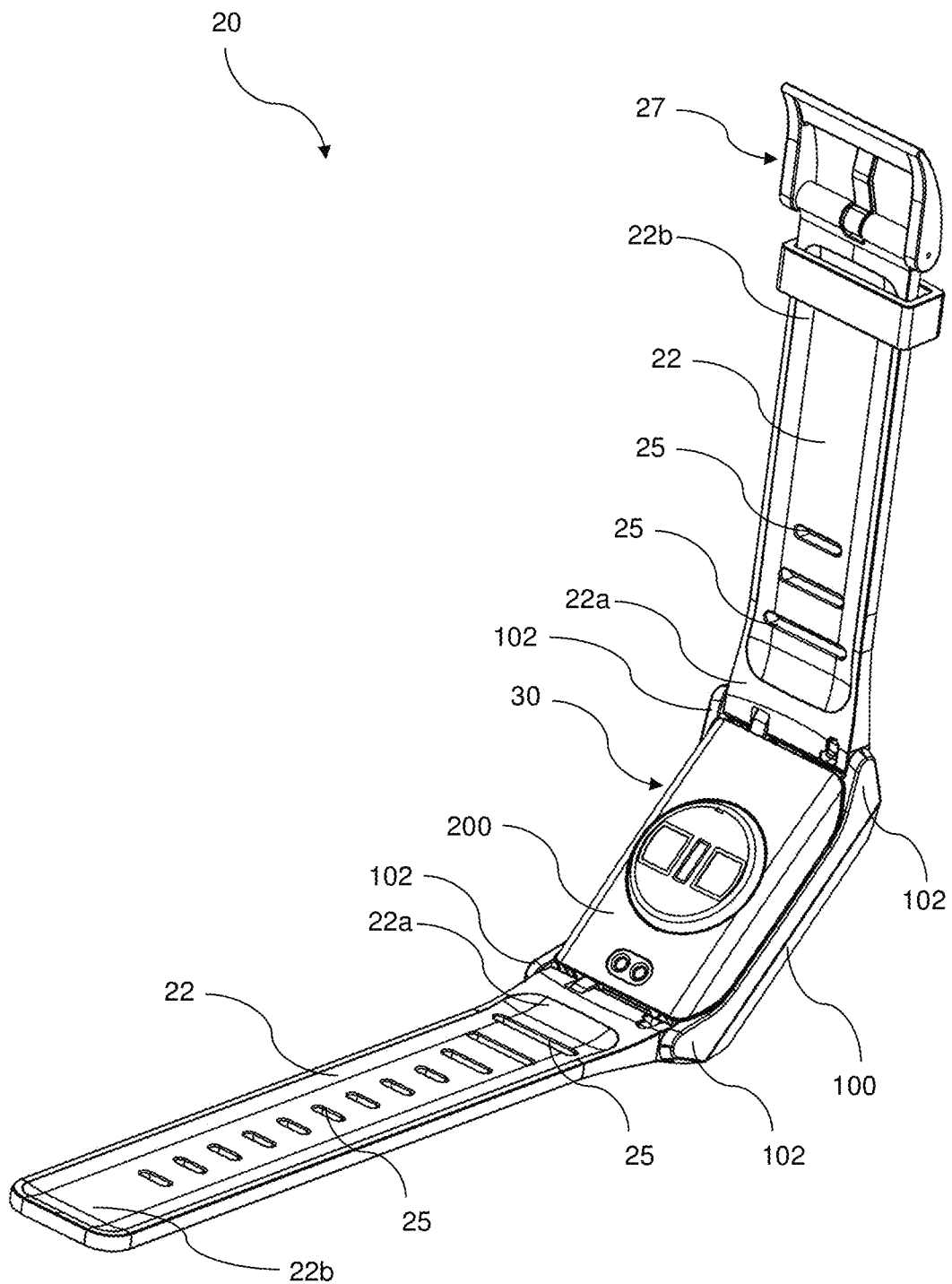

In some embodiments as shown in FIG. 1D, the strap fastener 26 is engaged or attached to a clasp 27a with a latch pin 27b through the strap fastener 26. The latch pin 27b may be separable from the strap fastener 26 for removing the clasp 27a. The clasp 27a may have a protrusion portion engageable with any one of the plurality of holes 24 of the opposite strap 22 for circumscribing or enclosing the user's wrist. Alternatively, these parts may be replaced with a standard wristwatch buckle 27 as shown in FIG. 2A and FIG. 2B.

In some embodiments as shown in FIG. 1B to FIG. 1D, the holes 24 along one of the straps 22 have identical dimensions and shape. For example, all the holes 24 along the strap 22 are circular with the same diameter. In some other embodiments as shown in FIG. 2A and FIG. 2B, the holes 24 along one or both of the straps 22 are elongated, i.e. shaped in the form of slots 25, and some of the slots 25 have different dimensions from the others. For each strap, the slot 25 nearest the proximal end 22a of the strap 22 is the longest and the slot 25 near the distal end 22b of the strap 22 is the shortest, such that the lengths of the slots 25 decrease gradually from the proximal end 22a to the distal end 22b. In one example, from the proximal end 22a to the distal end 22b, each slot 25 is longer than the next slot 25 such that all the slots 25 have different lengths. In another example, some of the slots 25 have identical lengths, such as if the lengths decrease after every pair of consecutive slots 25. Additionally, the spaces between every pair of consecutive slots 25 may be identical, or the slots 25 may be randomly spaced apart. The slots 25 may be present in one or both of the straps 22 and the arrangement of the slots 25 enhances breathability when the physiological device 20 is worn on the user's wrist. The user may also prefer the slots 25 to be arranged in some pattern so as to more easily identify his/her personal physiological device 20. The straps 22 may be imprinted or engraved with the user's signature/insignia 29 for easier identification.

With reference to FIG. 1A, each strap 22 includes an extended portion 22c disposed at or near the proximal end 22a thereof. The extended portion 22c may be chamfered or filleted to provide comfort to the physiological device 20 is worn. A gap 28 is formed between the extended portion 22c and the head assembly 30 when the physiological device 20 is worn on the user's wrist. The extended portions 22c may provide a snug fit to further lock and prevent the physiological device 20 from traversing along the length of the user's arm. When removed from the user's wrist, the straps 22 are unfastened and the physiological device 20 may be placed on a surface such as a table, the weight of the head assembly 30 weighs down and reduces the gaps 28. The extended portions 22c engages the head assembly 30 and prevents the head assembly 30 from contacting the surface, thereby providing greater stability when the physiological device 20 is placed on the surface. Additionally, the user may display and review the outputs from the physiological device 20 in a parallel eye level view.

As stated above, the straps 22 are removably attached to the lugs 102. It will be appreciated that the attachment of the straps 22 to the lugs 102 is similar or analogous to that of wristwatch straps and lugs. In one embodiment with reference to FIG. 3A, one or both straps 22 includes a fastening pin 23a at the proximal end 22a thereof for engagement with the lugs 102 to thereby attach the straps 22. One of the lugs 102 has a hole for receiving the fastening pin 23a. The fastening pin 23a is retractable, such as by spring-loading, so that the fastening pin 23a can be easily unfastened from the hole to thereby detach the straps 22. This allows for quick release, e.g. by clipping, latching, and/or snapping, for interchanging the straps 22 or replacing with personalized straps 22.

Figure 3A:
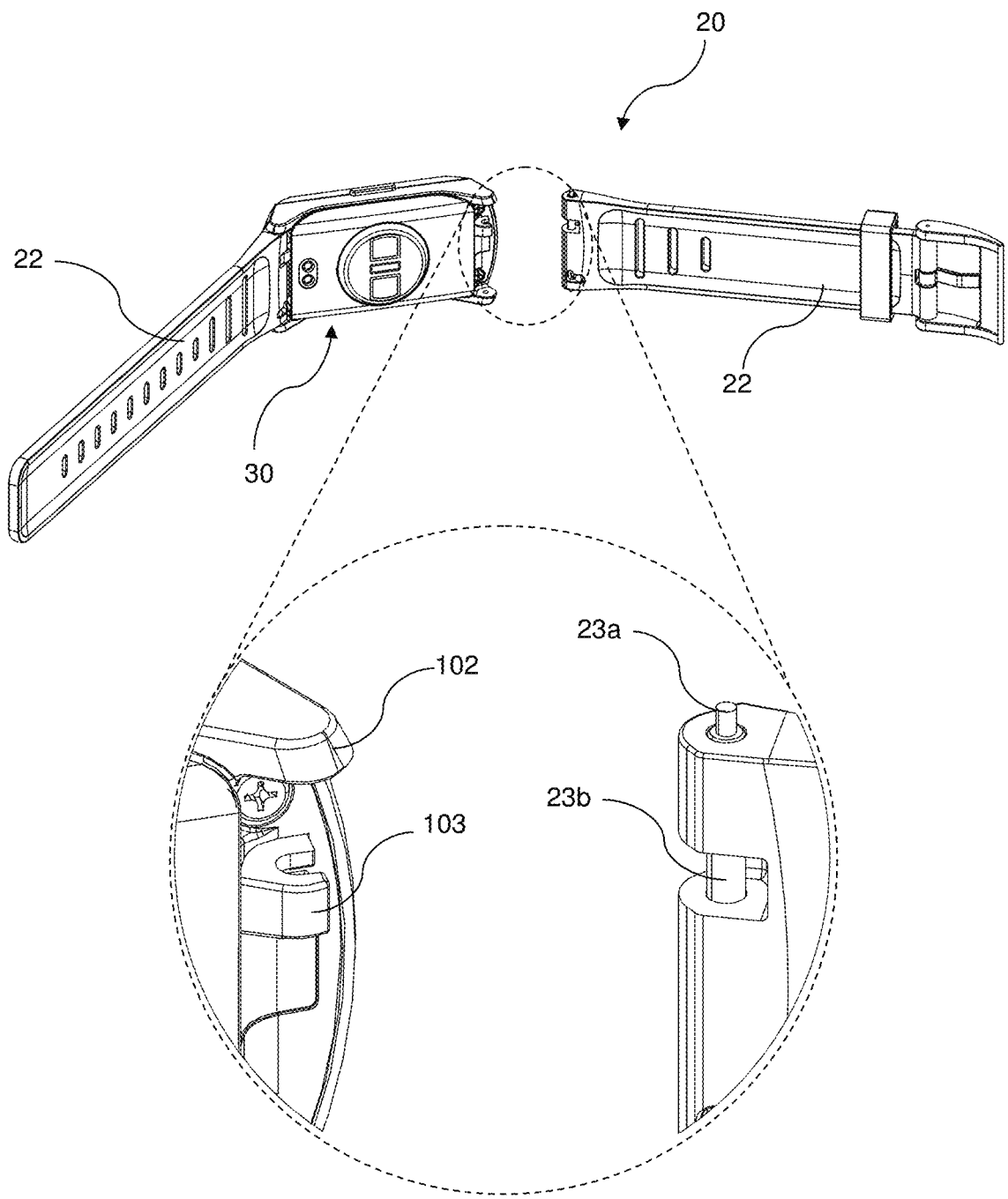
FIG. 3A illustrates a detail view of the wearable physiological device, in accordance with an embodiment of the present disclosure.
Figure 3B:
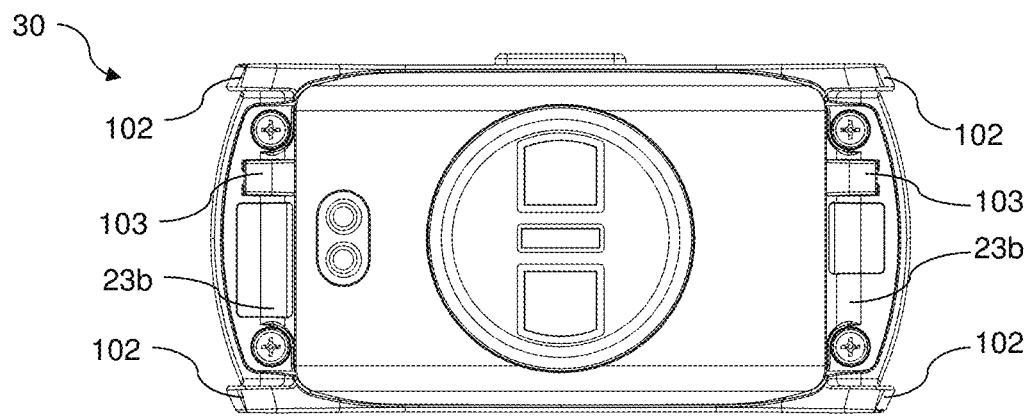
FIG. 3B to FIG. 3D illustrate a bottom view of the wearable physiological device, in accordance with some embodiments of the present disclosure.
Figure 3C:
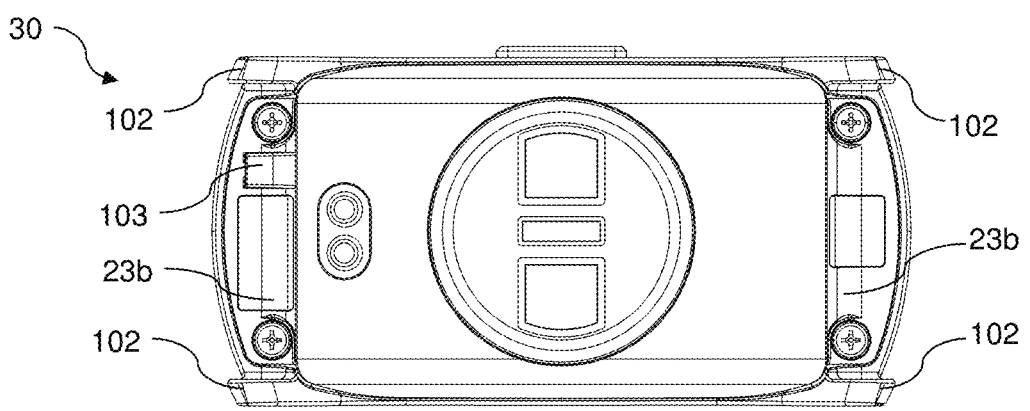
Figure 3D:
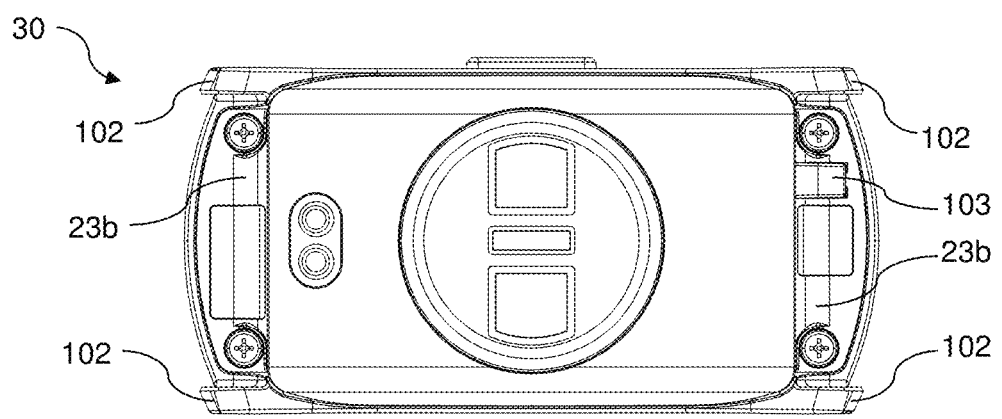

Also shown in FIG. 3A, the first housing assembly 100 includes an engagement element 103 disposed at the lugs 102, specifically between one or both pairs of the lugs 102. One or both straps 22 includes an engagement element 23b at the proximal end 22a thereof for engagement with the respective engagement element 103. The engagement elements 23b disposed at the strap 22 and the engagement element 103 disposed at the first housing assembly 100 are matingly engageable with each other, similar to engagements between standard male and female fasteners known to the skilled person. Additionally, the engagement elements 23b and 103 have different designs and configurations such that the engagement element 23b having a particular configuration uniquely matched and aligned to the engagement element 103 having a particular configuration. FIG. 3A illustrates an example of the configurations of the engagement elements 23b and 103 that are uniquely matched and aligned to each other. Accordingly, if the user has the physiological device 20 with particular configurations of the engagement elements 23b and 103, the user may replace the straps 22 with other straps 22 having the same engagement elements 23b. This may encourage the user to purchase authentic straps 22 from the original manufacturer instead of getting imitation straps 22 which may not fit well, or at all, with the user's existing physiological device 20. FIG. 3B to FIG. 3D illustrate other configurations of the engagement elements 103. It will be appreciated that the straps 22 will have matching engagement elements 23b for mating engagement with the engagement elements 103. It will also be appreciated that use of such matching engagement elements 23b and 103 may be on only one strap 22 or both straps 22.

With reference to FIG. 4A to FIG. 4D, the head assembly 30 includes the first housing assembly 100 and second housing assembly 200 removably coupled to each other. The first housing assembly 100 includes a first housing body 104 and the second housing assembly 200 includes a second housing body 202, wherein the second housing body 202 is disposed below the first housing body 104 and removably coupled thereto. The first housing assembly 100 further includes a user interface assembly 106 attached or coupled to the first housing body 104.

Figure 4A:
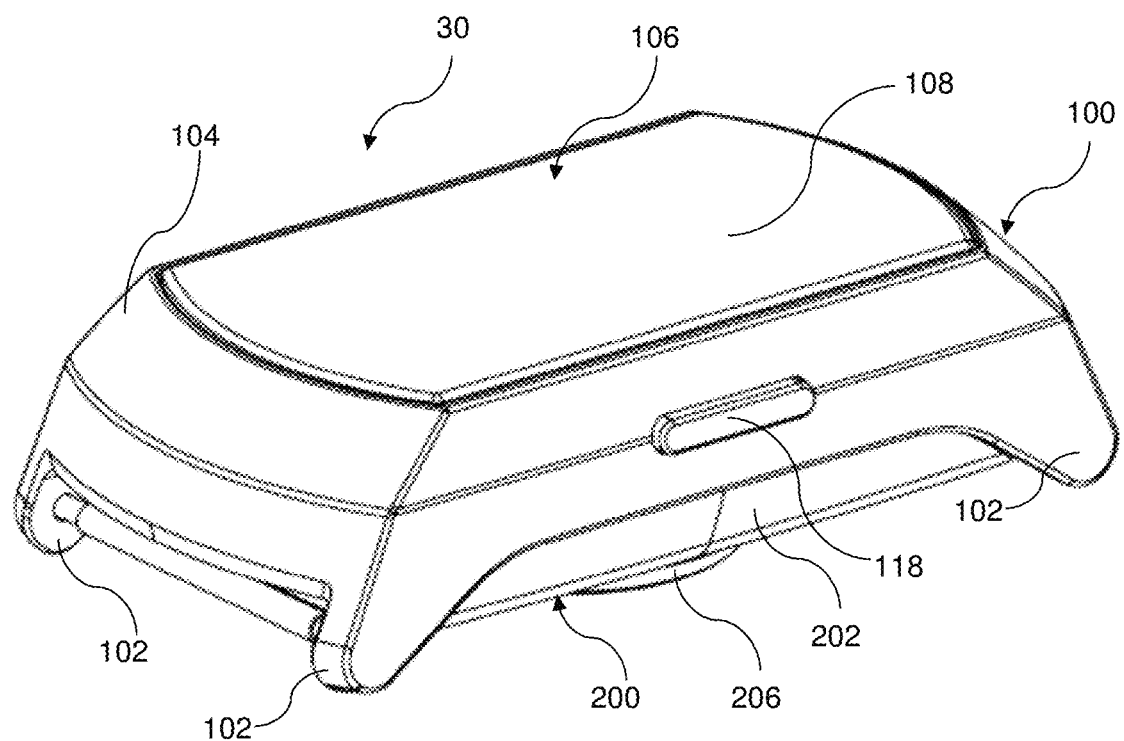
FIG. 4A to FIG. 4D illustrate various views of a head assembly of the wearable physiological device, in accordance with an embodiment of the present disclosure.
Figure 4B:
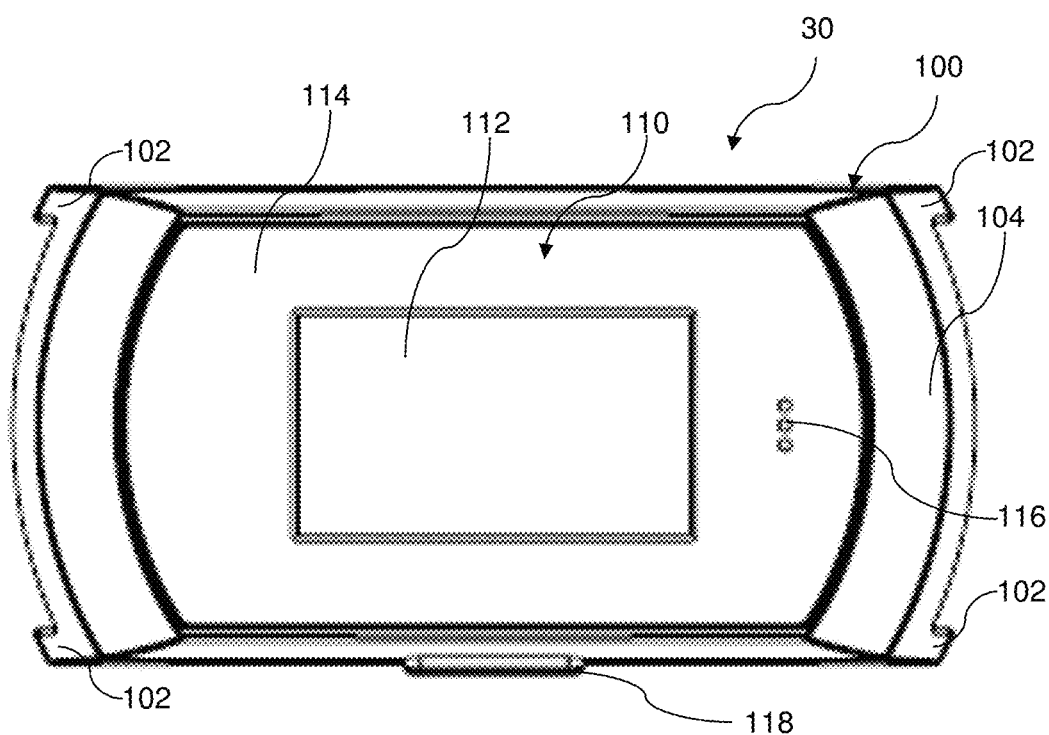
Figure 4C:
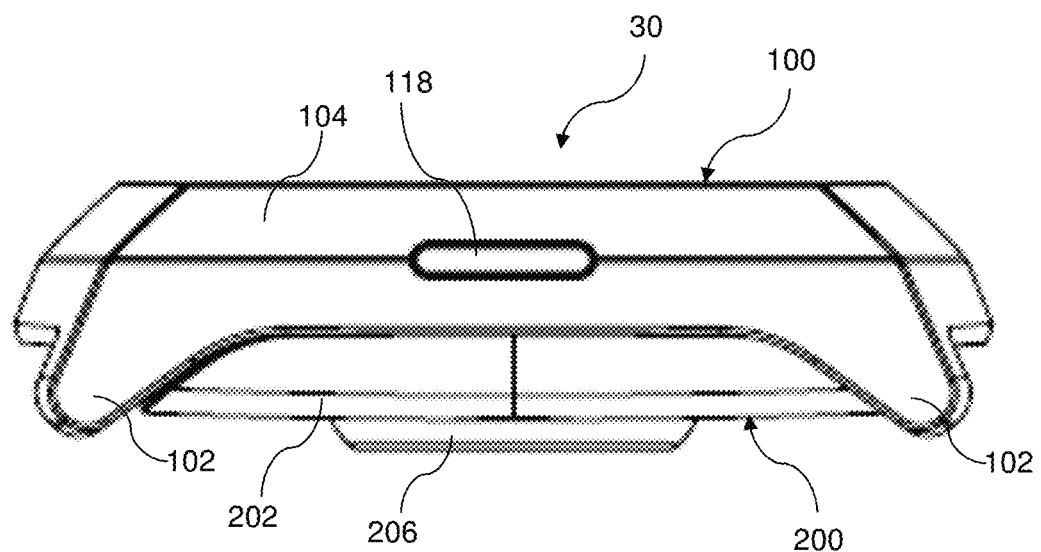
Figure 4D:
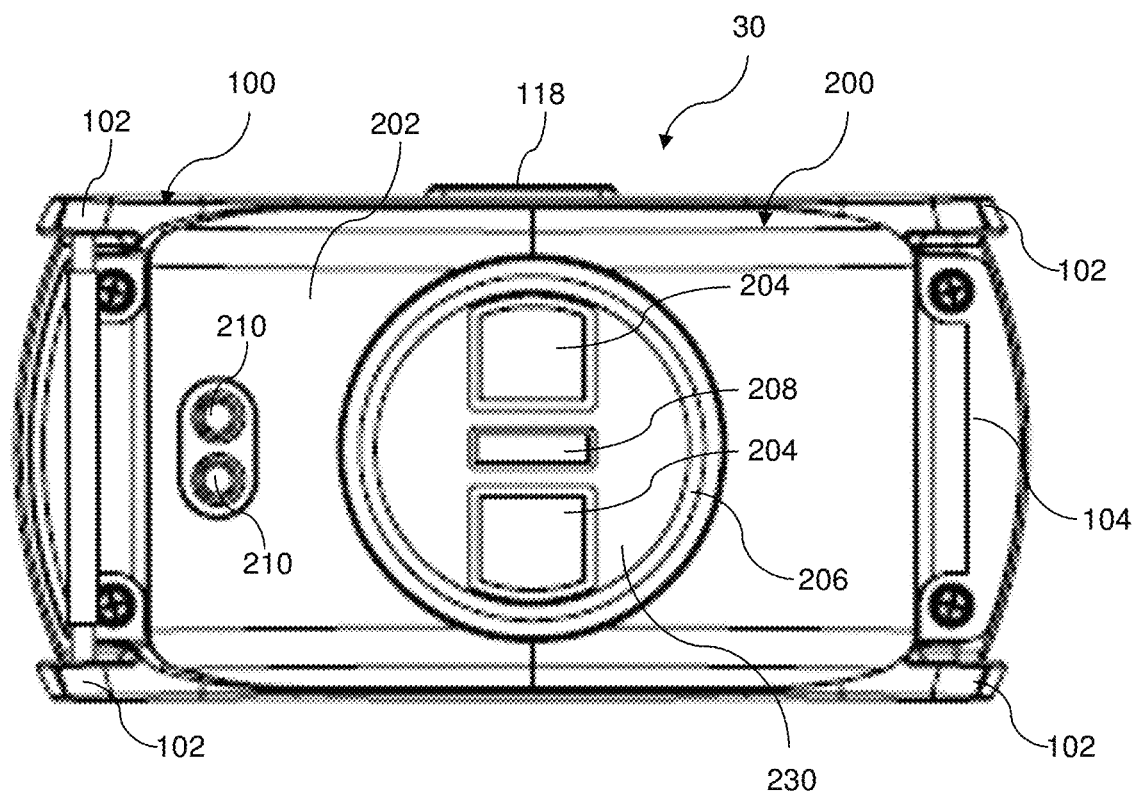

The user interface assembly 106 includes a display unit 108 attached to or coupled to an upper portion of the first housing body 104. The display unit 108 presents a screen 110 that provides a user interface for the user to control the physiological device 20. In one embodiment, the entire screen 110 is configured to receive control inputs from the user. In another embodiment as shown in FIG. 4B, the screen 110 is separated into a user interface area 112 and an inactive area 114. The user interface area 112 is configured to receive control inputs from the user, while the inactive area 114 is non-responsive to user inputs. The display unit 108 may be configured for touch gesture operations by the user on the screen 110. For example, the user is able to perform various operations by touch gestures on the user interface area 112 of the screen 110. The non-interactive area 114 may provide the user with relevant information in response to these touch operations.

The user interface assembly 106 may further include a set of illumination elements 116, such as light-emitting diodes (LEDs), for communicating visual signals, e.g. colour indications, to the user. The display unit 108 may be disposed with a filter portion for holding or laying different filter elements of different colours. The filter portion is thus cooperable with the illumination elements 116 to obtain different colour indications as desired by the user based on the choice of filter elements.

The user interface assembly 106 includes an actuator or button 118 disposed on an exterior or peripheral portion of the first housing body 104 for user operation, such as to toggle among different functions, of the physiological device 20. The different functions may by such as to provide the user with information on an activity e.g. distance and/or calorie count, sleep and/or stress condition that includes present or past state of mind.

The second housing assembly 200 includes a set of physiological sensors 204 disposed on a lower portion of the second housing body 202. Particularly, the lower portion of the second housing body 202 refers to a boss portion 206 that protrudes below the second housing body 202. The physiological sensors 204 are disposed on the boss portion 206 such that they are arranged to contact the user's skin (or at least being substantially proximate thereto) when the user is wearing the physiological device 20. The physiological sensors 204 are configured for measuring physiological signals from the user wearing the physiological device 20. These physiological signals include one or more of, but are not limited to, heart rate, blood pressure, photoplethysmogram (PPG) signals, and body temperature. In one embodiment, the physiological sensors 204 include one or more photodiode sensors for measuring PPG signals from the user's blood vessels. The second housing assembly 200 may further include an illumination element 208, e.g. an LED, to complement the photodiode sensors. Particularly, the user's skin is illuminated by the illumination element 208 and the photodiode sensors measure changes in light absorption. In another embodiment, the physiological sensors 204 include one or more temperature sensors for measuring body temperature of the user. It will be appreciated that the physiological sensors 204 may include one or more different types to be used in combination with one another to measure various types of physiological signals and data from the user. The measured physiological signals and data are stored on a database residing within the physiological device 20. In another example, the measured physiological signals and data may be streamed on-the-fly when connected to an electronic device separate from the physiological device 20. This electronic device may be a computer, mobile phone, or some remote server having a database residing therein for receiving and storing the physiological signals and data.

Figure 5:
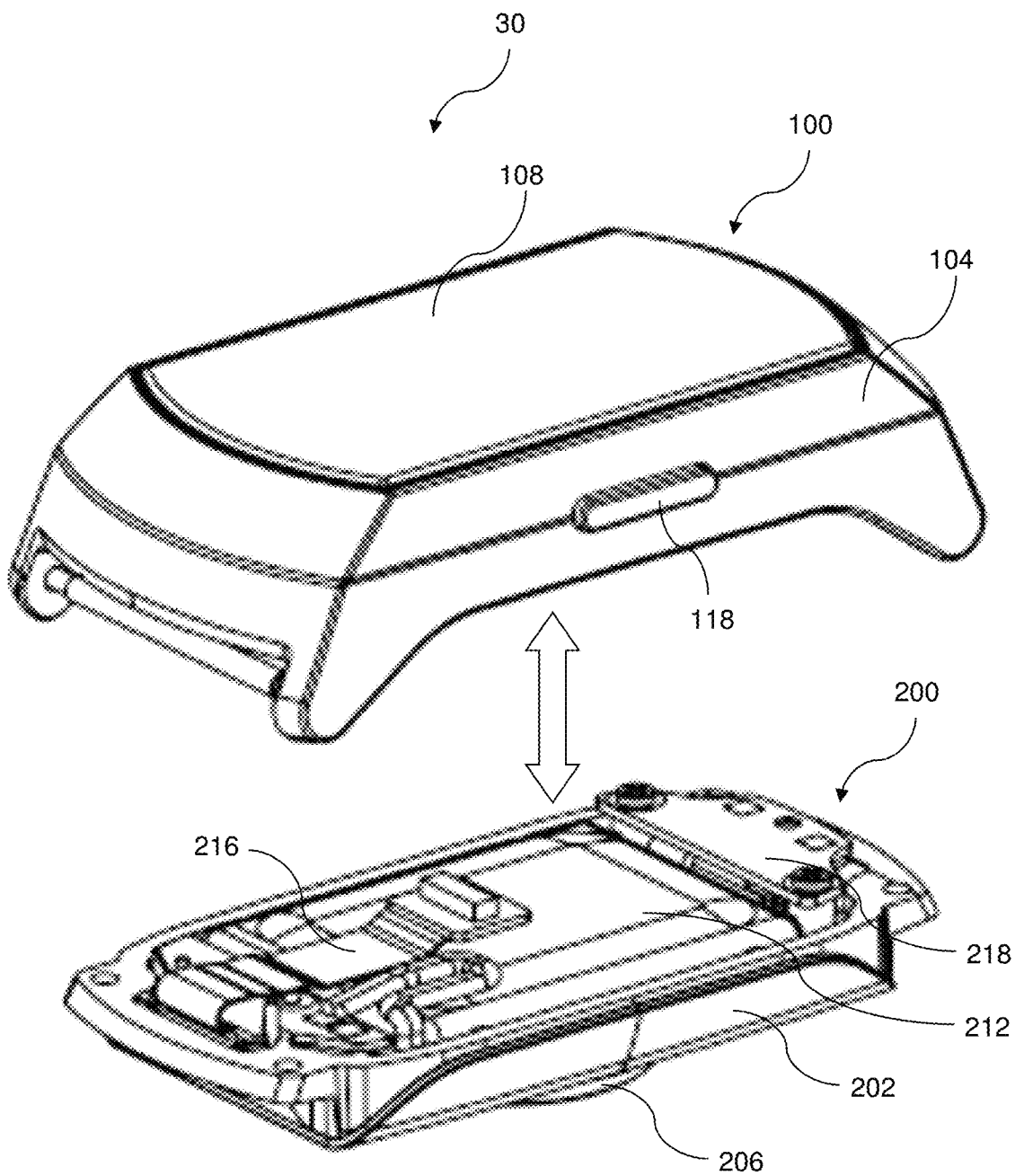
FIG. 5 illustrates an exploded view of the head assembly, in accordance with an embodiment of the present disclosure.

The second housing assembly 200 includes a set of electrical or charge contacts/pads 210 disposed on the lower portion of the second housing body 202. With reference to FIG. 5 illustrating an exploded view of the head assembly 30 wherein the second housing assembly 200 is removed or decoupled from the first housing assembly 100, the second housing assembly 200 includes a removable battery 212 disposed within the second housing body 202, the battery 212 for powering the physiological device 20. In one embodiment, an old battery 212 may be removed from the second housing body 202, and a new battery 212 simply inserted into the second housing body 202. In another embodiment, the new battery 212 is inserted into the second housing body 202 and soldered using standard soldering tools. The battery 212 may be chargeable, e.g. a lithium-ion polymer battery, and the electrical contacts 210 are connectable to an electrical supply for charging the battery 212. It will be appreciated that the physiological device 20 may be powered directly from the electrical supply via the electrical contacts 210 in the absence of the battery 212, such as when the battery 212 is damaged and removed from the second housing body 202.

Figure 6:
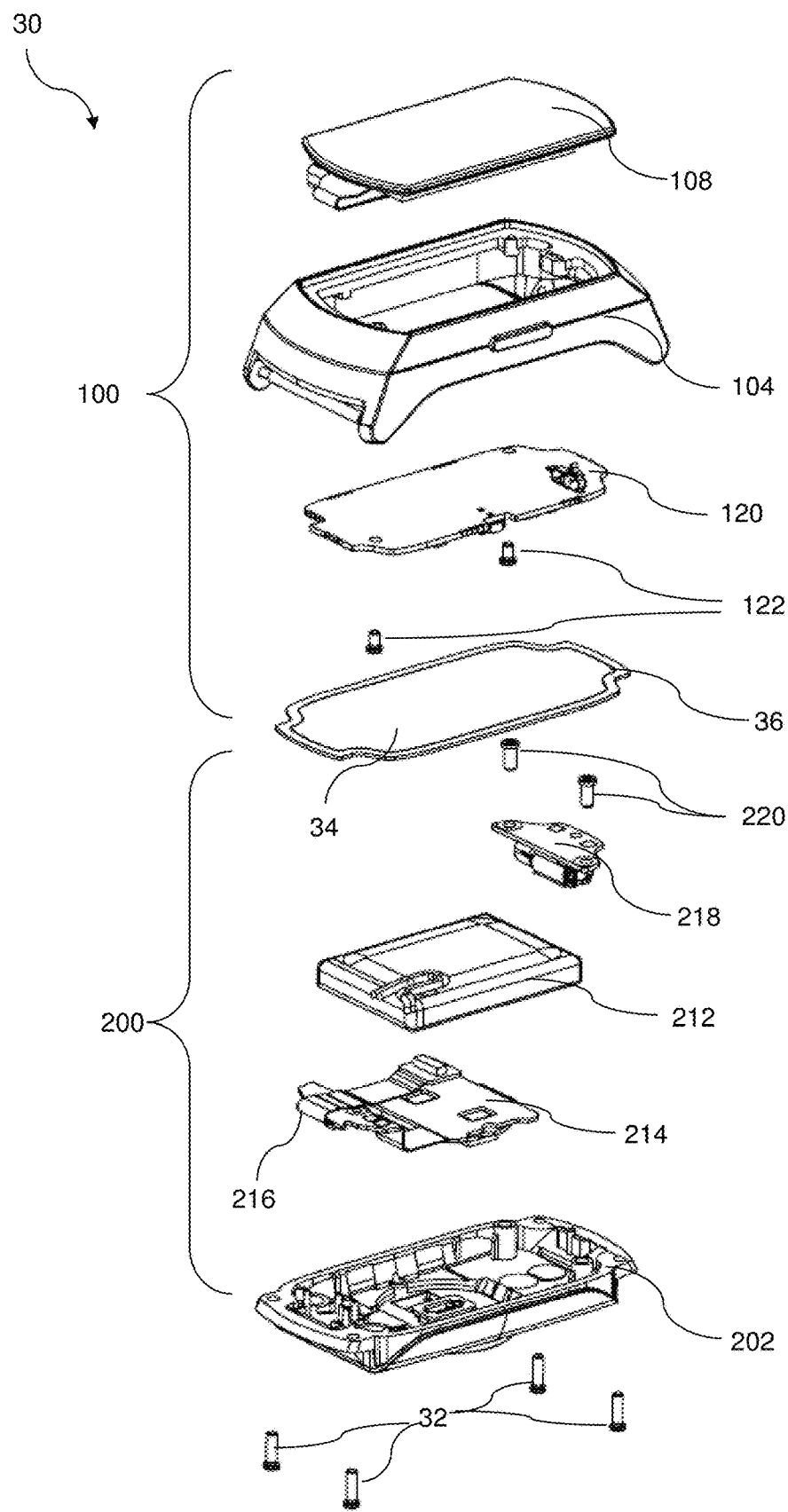
FIG. 6 illustrates another exploded view of the head assembly, in accordance with an embodiment of the present disclosure.

Further with reference to FIG. 6 illustrating another exploded view of the head assembly 30, the first housing assembly 100 and second housing assembly 200 are removably coupled together via a set of fasteners 32. The fasteners 32 may be screws or bolts that can be removed by the user with common household tools such as a screwdriver. Accordingly, the first housing assembly 100 and second housing assembly 200 can be easily disassembled and reassembled by the user.

The first housing assembly 100 includes a first circuit assembly 120 removably coupled to the first housing body 104. The second housing assembly 200 includes a second circuit assembly 214 removably coupled to the second housing body 202. Each of the first circuit assembly 120 and second circuit assembly 214 includes a printed circuit board (PCB) that supports and electrically connects various electrical/electronic components, as will be readily understood by the skilled person.

In some embodiments, the first circuit assembly 120 is coupled to the first housing body 104 and is disposed below the user interface assembly 106. The user interface assembly 106 is also communicatively connected to the first circuit assembly 120, such that operations performed by the user with the user interface assembly 106, e.g. the user interface area 112 and actuator 118, are communicated to the first circuit assembly 120 for processing. In one embodiment, the first circuit assembly 120 is removably coupled to the first housing body 104 with a set of fasteners 122, e.g. screws, allowing the user to easily disassemble and reassemble the first circuit assembly 120.

In some embodiments, the second circuit assembly 214 is coupled to the second housing body 202. Specifically, the second circuit assembly 214 is removably coupled, e.g. by an attachment or latching mechanism known to the skilled person, to an internal surface of the second housing body 202. The second circuit assembly 214 includes the physiological sensors 204, illumination element 208, and removable battery 212. The physiological sensors 204 are disposed on one side of the second circuit assembly 214 and the battery 212 is disposed on the reverse side of the second circuit assembly 214.

The second circuit assembly 214 includes a flexible connector 216 communicatively connecting the second circuit assembly 214 to the first circuit assembly 120. Specifically, one end of the flexible connector 216 is connected to the second circuit assembly 214 and another end of the flexible connector 216 is connected to the first circuit assembly 120 upon assembling of the first housing assembly 100 and second housing assembly 200 together. The flexible connector 216 is a flexible printed circuit (FPC) that enables electronic communication, including data and electricity, between the first circuit assembly 120 and second circuit assembly 214. For example, physiological signals measured by the physiological sensors 204 are communicable from the second circuit assembly 214 to the first circuit assembly 120 via the flexible connector 216, and subsequently processed and displayed to the user on the display unit 108. Electricity from the battery 212 is also conducted from the electrical contacts 210 to the second circuit assembly 214 and subsequently to the first circuit assembly 120.

In one embodiment, the second housing assembly 200 includes a haptic device 218 and optionally an accelerometer coupled to the second housing body 202. The haptic device 218 includes a haptic motor that provides kinesthetic communication to the user, such as by applying forces, vibrations, and/or motions to the user when the user is wearing the physiological device 20. For example, the kinesthetic communication may be in the form of haptic feedback, e.g. force or vibrational feedback, to the user in response to various results derived from the physiological signals. The haptic device 218 may be removably coupled to the second housing body 202 with a set of fasteners 220, e.g. screws, allowing the user to easily disassemble and reassemble the haptic device 218.

In some embodiments, the wearable physiological device 20 includes an intermediate support 34 disposed between the first housing assembly 100 and second housing assembly 200. The intermediate support 34 is arranged to surround a periphery of the first housing body 104 and second housing body 202 for inhibiting/reducing liquid ingress or seepage, into the first housing assembly 100 and second housing assembly 200, thereby providing a water resistance feature to the physiological device 20. Specifically, the intermediate support 34 includes a sealing element 36, disposed around the periphery of the intermediate support 34, which seals the space between the first housing assembly 100 and second housing assembly 200 upon assembling and merging of the first housing assembly 100 and second housing assembly 200.

Figure 7A:
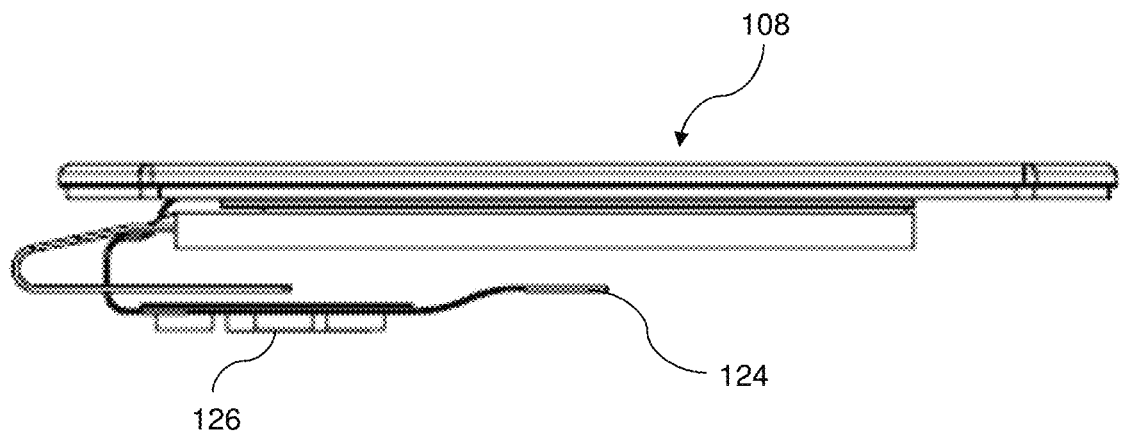
FIG. 7A illustrates a cross-sectional view of a display unit of the head assembly, in accordance with an embodiment of the present disclosure.

As shown in FIG. 7A illustrating a cross-sectional view of the display unit 108, the first housing assembly 100 includes a flexible connector 124 which is a FPC that enables electronic communication between the first circuit assembly 120 and display unit 108. Specifically, one end of the flexible connector 124 is connected to the first circuit assembly 120 and another end of the flexible connector 124 is connected to the display unit 108. The flexible connector 124 includes a set of touch controllers or touch control modules/components 126 for communicating touch gestures made on the display unit 108 to the first circuit assembly 120.

In one embodiment, the illumination elements 116 are disposed on the display unit 108 for providing visual indications to the user. In another embodiment, the illumination elements 116 are disposed on the first circuit assembly 120. The display unit 108 includes one or more apertures aligned with the illumination elements 116 to allow light from the illumination elements 116 to pass through.

Figure 7B:
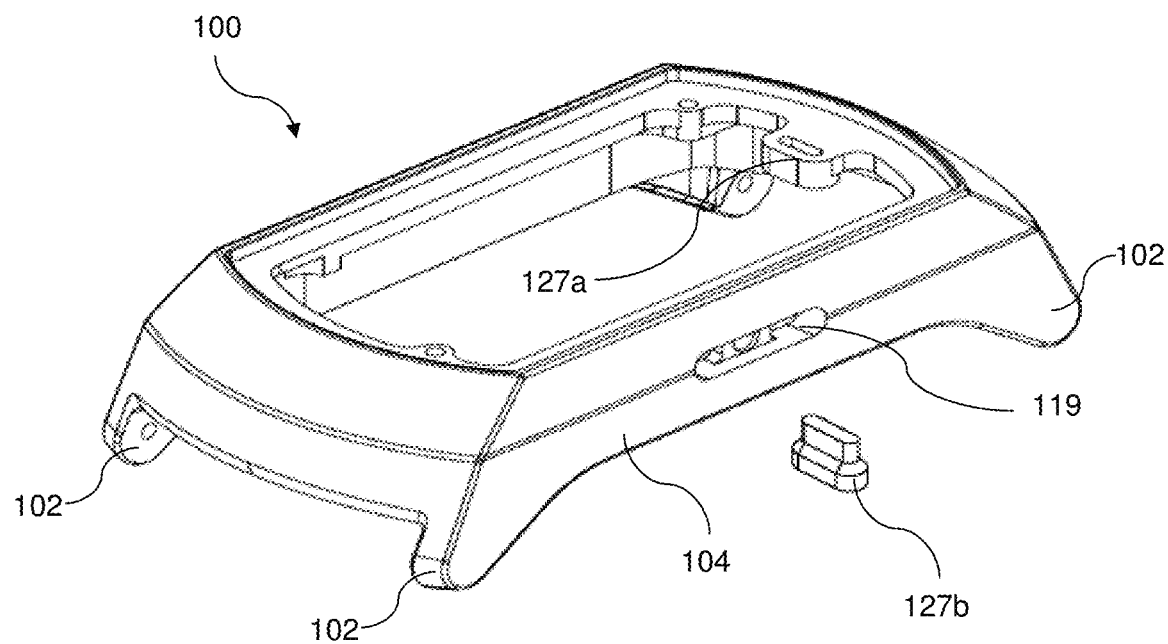
FIG. 7B and FIG. 7C illustrate various views of a first housing assembly of the head assembly, in accordance with an embodiment of the present disclosure.
Figure 7C:
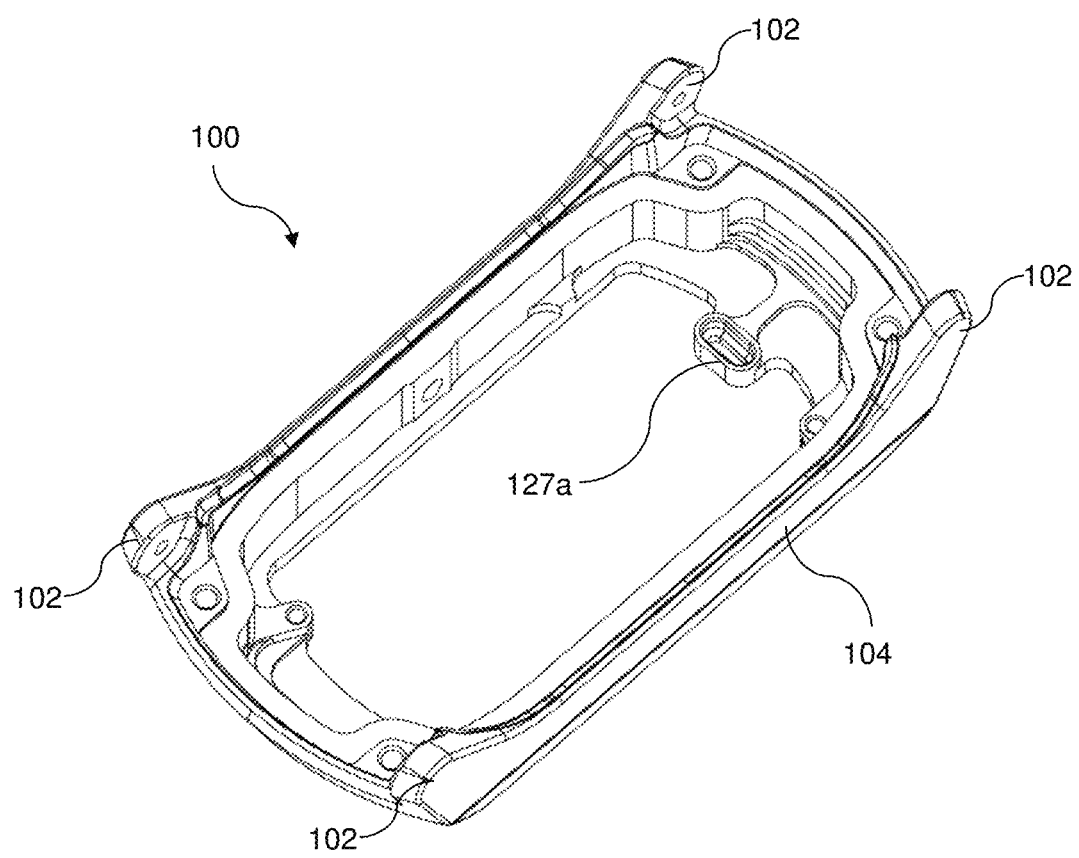

In some embodiments with reference to FIG. 7B and FIG. 7C, the first housing body 104 includes one or more slots or receptacles 127a to receive a diffuser 127b. The slot 127a is aligned with the illumination elements 116 such that the diffuser 127b is arranged to evenly distribute light from the illumination elements 116. Furthermore, the diffuser 127b may evenly distribute heat generated by the illumination elements 116.

Figure 7D:
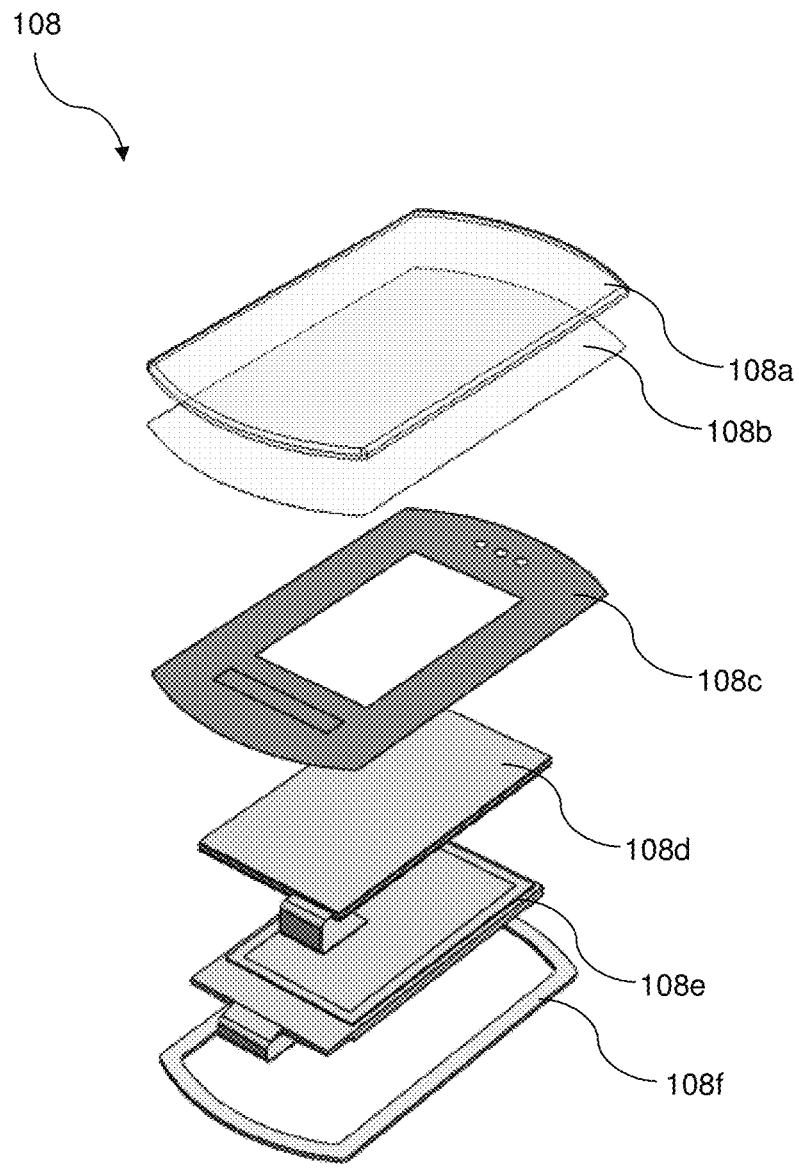
FIG. 7D illustrates an exploded view of the display unit, in accordance with an embodiment of the present disclosure.

With reference to FIG. 7D illustrating an exploded view of the display unit 108, the display unit 108 includes various components in a layered arrangement, such that these components/layers can be assembled by stacking up in a systematic or modular manner. The components/layers may be assembled together by adhesive/bonding materials as will be apparent to the skilled person. The display unit 108 includes a cover layer 108a to protect the other internal layers of the display unit 108. The user interfaces with the physiological device 20 via the display unit 108, e.g. by touch gestures on the cover layer 108a. The cover layer 108 may be made of a glass material that is scratch-resistant and shatterproof. It will be appreciated that the cover layer 108 may be made of other materials, such as a plastic or a composite material, as will be readily known to the skilled person. The display unit 108 includes a tint layer/panel 108b to mask away glare, such as sunlight glare when the physiological device 20 is used outdoors. The display unit 108 includes a mask or logo layer/panel 108c for providing a fixed or predefined space for display visualization. The fixed or predefined space includes a boundary space corresponding to the inactive area 114 as shown in FIG. 4B. The display unit 108 includes an ITO (indium tin oxide) layer/panel 108d for output display based on information received from the first circuit assembly 120. The display unit 108 includes an OLED (organic light-emitting diode) layer/panel 108e which is an emissive electroluminescent layer that emits light in response to an electric current. The layer/panel 108e may alternatively be of another type of light-emitting layer, such as LED or Liquid Crystal Display (LCD). The layer/panel 108e may be of a flat or curved shape. The display unit 108 includes a support layer 108f for combining each of the other layers 108a to 108e to form into the display unit 108. In one embodiment, the support layer 108f has an adhesive material for combining the other layers 108a to 108e together. The support layer 108f also functions as a sealing element to prevent liquid or water ingress/seepage into the first housing assembly 100 via the display unit 108.

It will be appreciated that the display unit 108 may be modified to be without one or more of the layers 108a to 108f, and that the display unit 108 may similarly be modified to include additional layers or panels known to the skilled person. In one embodiment, the support layer 108f has an adhesive material for attaching the display unit 108 to the first housing body 104. In another embodiment, the display unit 108 is removably coupled to the first housing body 104 with an attachment or latching mechanism known to the skilled person, allowing the user to easily disassemble and reassemble the display unit 108.

Figure 8:
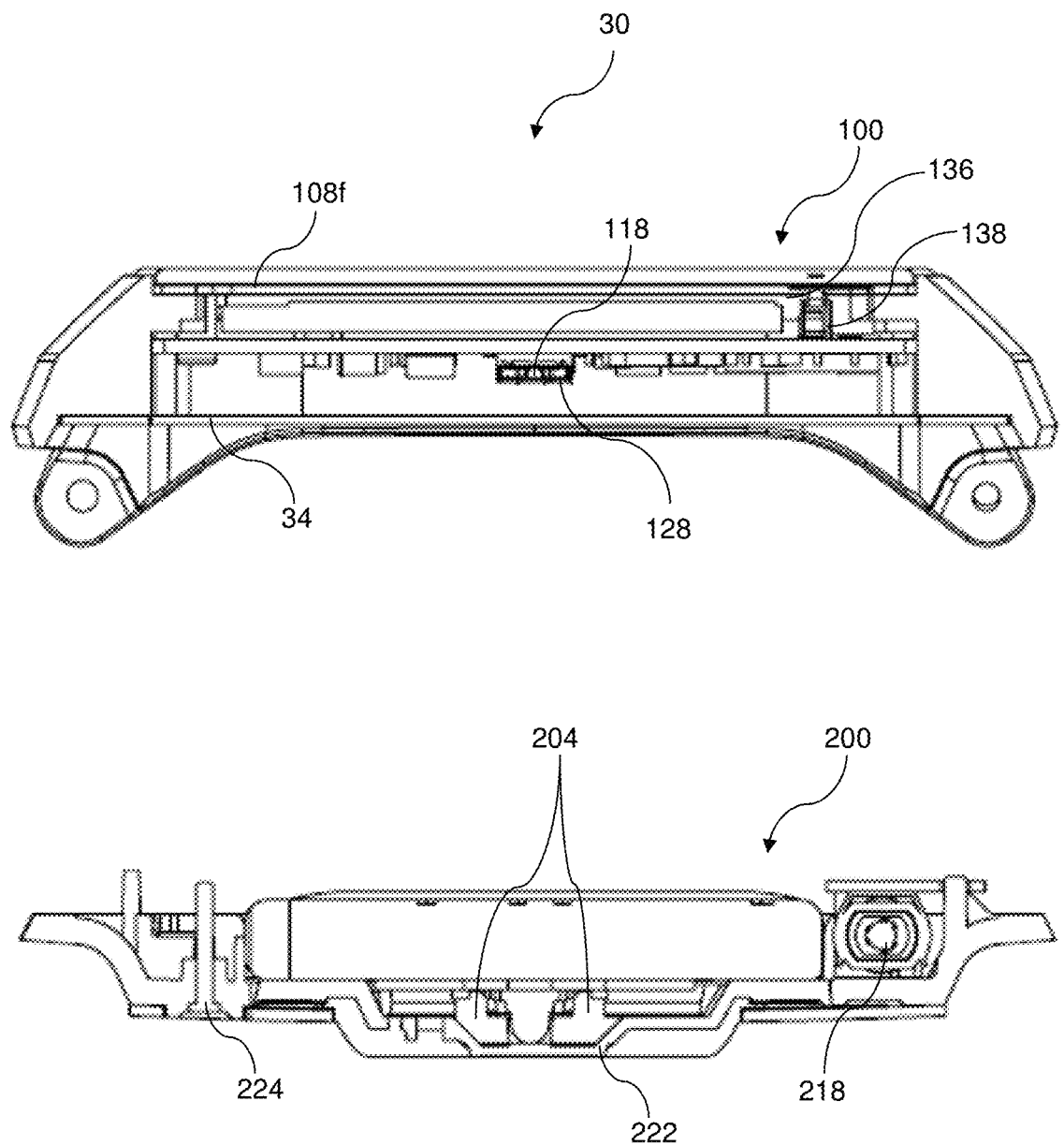
FIG. 8 illustrates a cross-sectional view of the head assembly in disassembled form, in accordance with an embodiment of the present disclosure.

With reference to FIG. 8 illustrating a cross-sectional view of the head assembly 30 in disassembled form, the head assembly 30 includes various sealing elements for preventing liquid or water ingress/seepage into the head assembly 30. For example, the second housing assembly 200 includes a sensor protective cover 222 for the physiological sensors 204. Specifically, the sensor protective cover 222 protects and seals the physiological sensors 204 from water ingress. The sensor protective cover 222 includes a transparent portion so that light can still be transmitted from the illumination element 208 to the skin and that physiological signals can be effectively measured. The transparent portion may have a magnifying effect to improve the quality of measurements. The magnifying effect may be achieved by adding one or more other optical elements, e.g. objective lens. The second housing assembly 200 may include a sealing cover 224 for the electrical contacts 210. The sealing cover 224 may be removed by the user when the battery 212 needs to be charged, and replace the sealing cover 224 during use of the physiological device 20 so as to maintain its water resistance.

Figure 9:
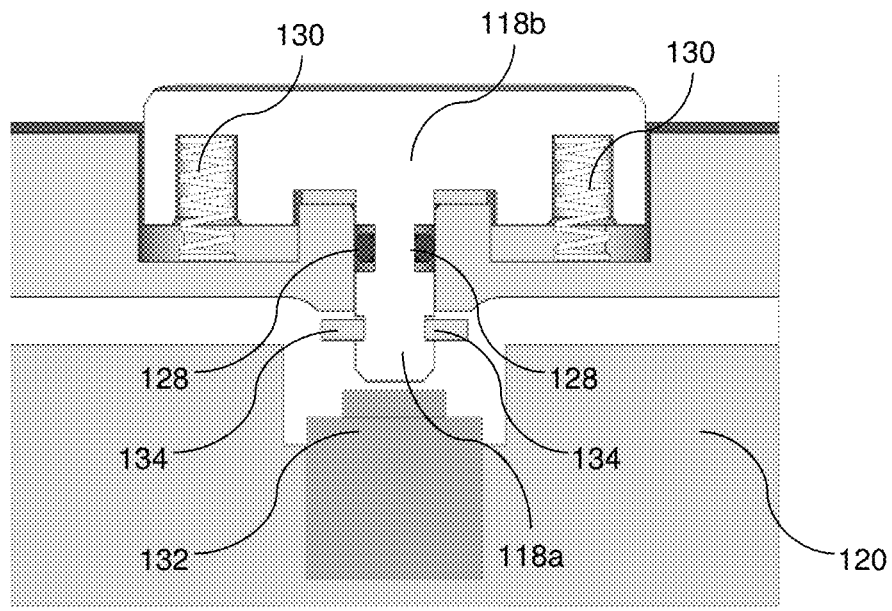
FIG. 9 illustrates a cross-sectional view of a region around an actuator of the head assembly, in accordance with an embodiment of the present disclosure.

In some embodiments, the first housing assembly 100 includes a sealing element 128 for the actuator 118. Referring to FIG. 9 illustrating a cross-sectional view of the region around the actuator 118, the sealing element 128 surrounding an inner actuating portion 118a. The inner actuating portion 118a is connected or integrally joined to an outer actuating portion 118b which is exposed for the user to operate. The sealing element 128 may be or includes an O-ring or toric joint which seals the inner actuating portion 118a to prevent liquid/water ingress/seepage into the first housing assembly 100.

The first housing assembly 100 includes a set of biasing mechanisms 130, e.g. compression springs, for biasing the actuator 118 back to the unactuated state after actuation by the user. Specifically, after the user depresses the outer actuating portion 118b, the inner actuating portion 118a actuates and contacts a switch module or component 132 of the first circuit assembly 120, thereby performing an operation or function on the wearable device 20. The biasing mechanisms 130 return the actuator 118 from the actuated state to the unactuated state. The inner actuating portion 118a is assembled into the first housing body 104 through a hole thereof and with appropriate engineering tolerance. The engineering tolerance is determined to align the inner actuating portion 118a with the hole and to improve axial stability of the actuator 118. The first housing assembly 100 includes a clip mechanism 134 for clipping the inner actuating portion 118a to prevent removal of the actuator 118 from the first housing assembly 100. In addition, the clip mechanism 134 may be separable from the first housing body 104 for removing the actuator 118, such as for replacing a damaged actuator 118.

In some embodiments, with reference to FIG. 8, the first housing assembly 100 includes a data communication module or component 136 communicatively connected to the first circuit assembly 120. Further with reference to the functional block diagram illustrated in FIG. 10, the wearable physiological device 20 is communicable with an electronic device 50 via the data communication module 136. The electronic device 50 may be a mobile device, such as mobile phone, smartphone, personal digital assistant (PDA), tablet, laptop, or computer. Optionally, the head assembly 30 includes a communication port for connecting to a communication cable which is in turn connectable to the electronic device 50, such as a USB (Universal Serial Bus) port for receiving a USB cable. Alternatively, the electronic device 50 is a remote server that is a physical or cloud data processing system and includes computers, laptops, minicomputers, mainframe computers, any non-transient and tangible machines that can execute a machine-readable code, cloud-based servers, distributed server networks, and a network of computer systems.

The communication between the physiological device 20 and electronic device 50 via the data communication module 136 may occur across a communication network, such as by wireless communication protocols, as will be readily understood by the skilled person. In one example, the communication network may be a short range, such as Wi-Fi, Bluetooth Low Energy (BLE), or Near Field Communication (NFC). In another example, the communication network may be long range, such as Local Area Network (LAN), Wireless Area Network (WAN), telecommunication network, cellular network, satellite network, or LoRa WAN (Long Range WAN).

As disclosed in various embodiments herein, the physiological device 20 is wearable on the user's wrist for monitoring of the user's physiological health. Specifically, the physiological sensors 204 measure physiological signals from the user's blood vessels and communicate the physiological signals to the second circuit assembly 214 and subsequently to the first circuit assembly 120 for processing. Each of the first circuit assembly 120 and second circuit assembly 214 includes a computer processor or microprocessor for performing said processing. The processed data may provide the user with various types of information, such as relating to the user's activity, sleep or stress condition, and the information is presented to the user via the display unit 108 and illumination elements 116. For example, the screen 110 may display one or more icons for presenting information to the user. The icons may relate to different situations, such as when the user is in a stress state, normal state, or when no data is obtained.

Additionally, the illumination elements 116 may provide visual indications to the user, such as of the user's stress condition or state. For example, if the illumination elements 116 illuminated in purple colour may represent an abnormal stress condition, while green colour may represent a normal condition. Other colours may indicate other information, such as lack of or inadequate physiological data from the sensors 204, or failure/malfunctioning of the sensors 204. As mentioned above, the illumination elements 106 may be replaced by the user with that of other colours.

The information may also be communicated from the physiological device 20 to the electronic device 50, such as for keeping data records of the user's activity/sleep/stress history. While not explicitly described herein, it will be appreciated that the head assembly 30 may be modified to include additional components, such as additional alert devices (sound and/or haptic). Some other components may include, but are not limited to, accelerometers, gyroscopes, and magnetometers.

Assembling/Disassembling the Wearable Physiological Device

The head assembly 30 is formed by assembling various parts or components together. Some of these components are removably coupled so that they can be replaced by the user. For example, the first housing assembly 100 and second housing assembly 200 are removably coupled together.

Figure 11:
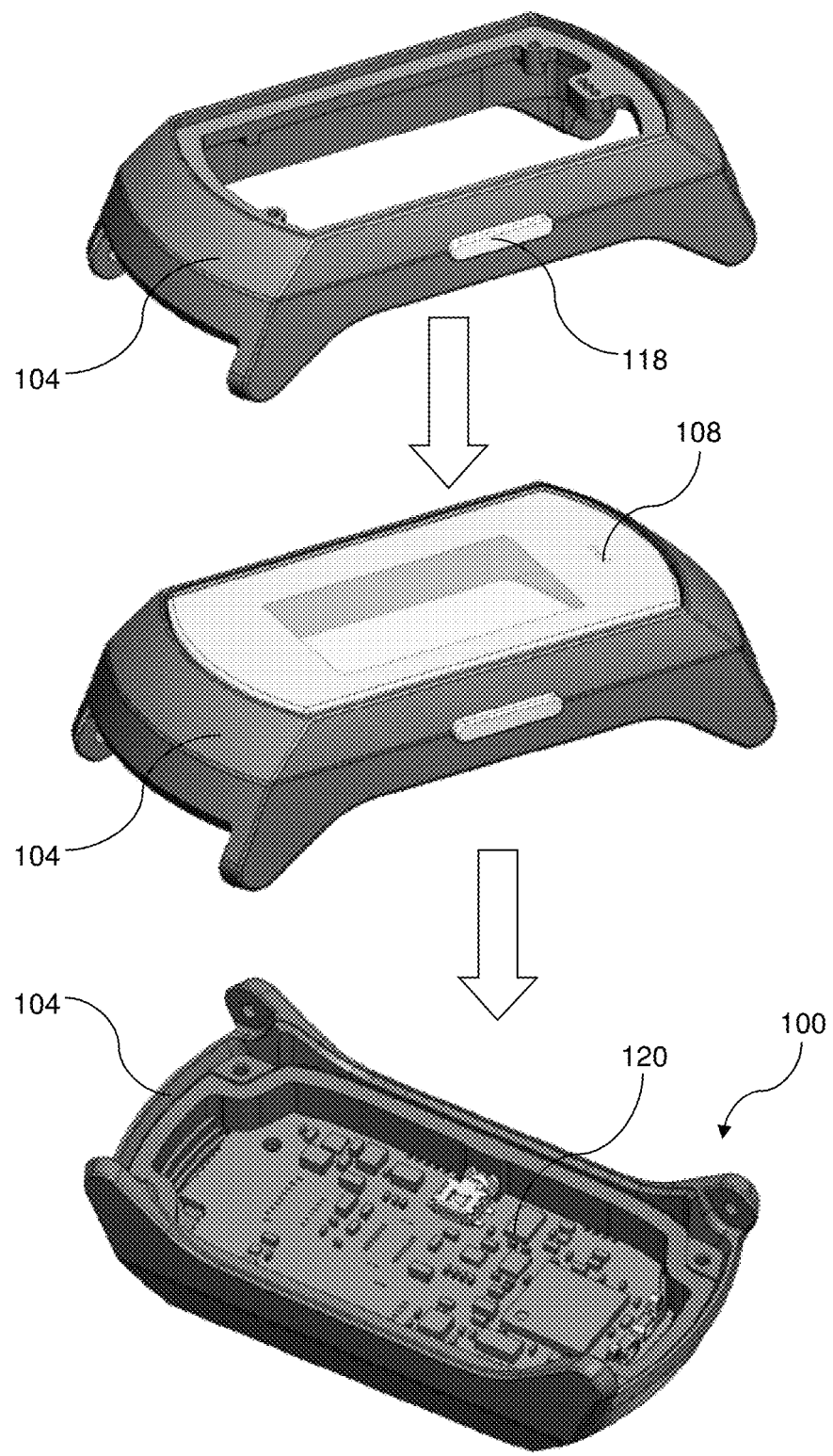
FIG. 11 illustrates assembling of a first housing assembly of the head assembly, in accordance with an embodiment of the present disclosure.

FIG. 11 illustrates the assembling of the first housing assembly 100. For purpose of brevity, only the main steps are described. The first housing body 104 may be formed by standard manufacturing technologies known to the skilled person. The first housing body 104 may be formed as a single integral body or from a plurality of structures/bodies joined together. The user interface assembly 106 is coupled to the first housing body 104. Specifically, the display unit 108 and actuator 118 are coupled to the first housing body 104. In one embodiment, the display unit 108 is coupled by an adhesive. In another embodiment, the display unit 108 is removably coupled by an attachment or latching mechanism. The first circuit assembly 120 is removably coupled to the first housing body 104, such as with a set of fasteners or screws 122. Accordingly, various components of the first housing assembly 100 are easily assembled together in a stacked or layered arrangement with minimal effort. It will be appreciated that disassembly can also be done easily in a reverse manner. For example, the first circuit assembly 120 may have to be removed/decoupled first before removing/decoupling the display unit 108.

Figure 12:
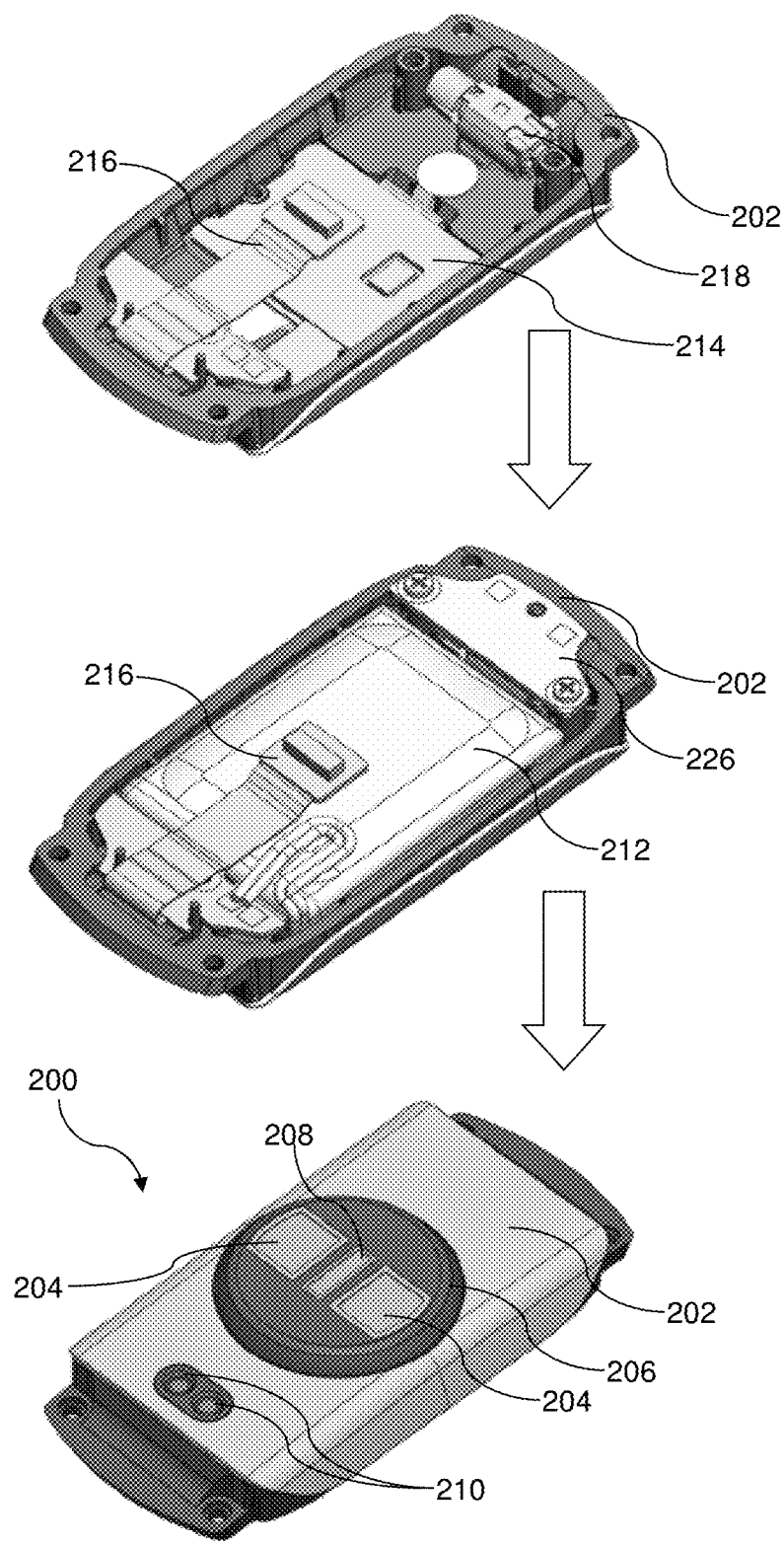
FIG. 12 illustrates assembling of a second housing assembly of the head assembly, in accordance with an embodiment of the present disclosure.

FIG. 12 illustrates the assembling of the second housing assembly 200. For purpose of brevity, only the main steps are described. The second housing body 202 may be formed by standard manufacturing technologies known to the skilled person. The second housing body 202 may be formed as a single integral body or from a plurality of structures/bodies joined together. The second circuit assembly 214 is removably coupled to the second housing body 202, such as with an attachment or latching mechanism. The haptic device 218 is also removably coupled to the second housing body 202, such as with fasteners/screws. The battery 212 is removably coupled to the second housing body 202 by disposing on the second circuit assembly 214. Specifically, one end of the flexible connector 216 is lifted and the battery 212 is disposed between the second circuit assembly 214 and the flexible connector 216. Optionally, a vibration absorber 226 is removably coupled to the second housing body 202, such as with fasteners/screws. The vibration absorber 226 is positioned to overlay the haptic device 218 so as to absorb or reduce vibrations caused by motion of the haptic device 218. Accordingly, various components of the second housing assembly 200 are easily assembled together in a stacked or layered arrangement with minimal effort. It will be appreciated that disassembly can also be done easily in a reverse manner. For example, the battery 212 may have to be removed/decoupled first before removing/decoupling the second circuit assembly 214.

Figure 13:
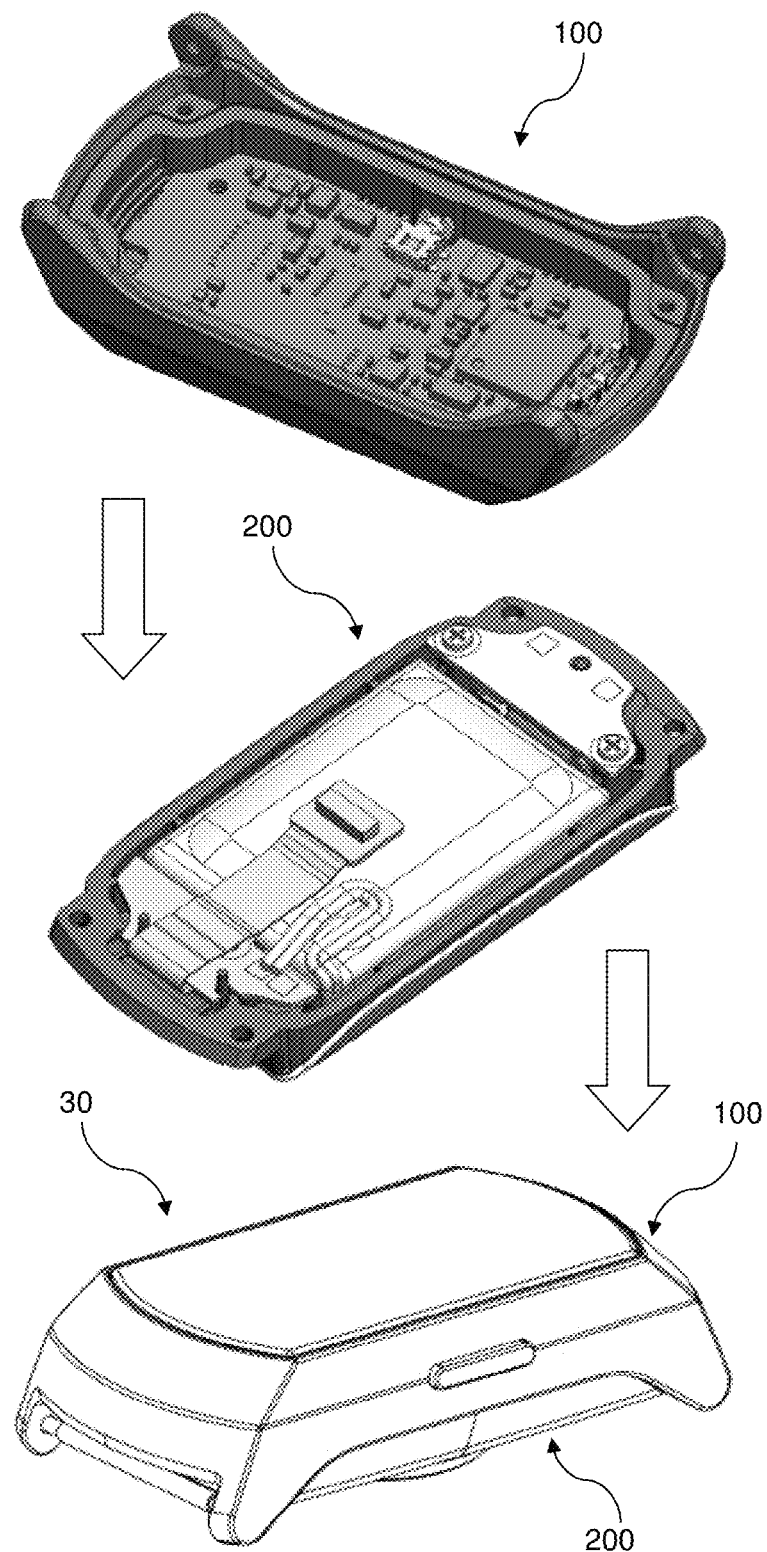
FIG. 13 illustrates assembling of the head assembly, in accordance with an embodiment of the present disclosure.

FIG. 13 illustrates the assembling of the first housing assembly 100 and second housing assembly 200 together. Specifically, the first housing assembly 100 and second housing assembly 200 are removably coupled together via a set of fasteners or screws. Upon said coupling, the flexible connector 216 connects the second circuit assembly 214 to the first circuit assembly 120 for communication therebetween.

To further simplify the assembly process, connections among components coupled to the first circuit assembly 120, such as the haptic device 218, are coupled with the use of spring fingers instead of cables. In addition, when the first housing assembly 100 and second housing assembly 200 are coupled together, there is only the flexible connector 216 to connect between them. This flexible connector 216 is easy to connect and does not require special tools.

Accordingly, the first housing assembly 100 and second housing assembly 200, as well as various components thereof, are easily assembled together in a stacked or layered arrangement with minimal effort. Various components of the head assembly 30 can thus be disassembled and reassembled by the user. These components can be easily replaced by the user if they become damaged or are worn out after prolonged use. Particularly, components in a constant active state, e.g. physiological sensors 204 and battery 212, have shorter lifespans than other components, and their operational performances are more easily affected by time.

Advantageously, it will not be necessary for the user to replace the entire physiological device 20 or head assembly 30 if only one or some components are damaged, thus reducing their expenditure on repairing the physiological device 20. The user is given more control of the physiological device 20 and this helps to extend the lifespan of the physiological device 20.

Furthermore, over time, some components may become obsolete and the user can replace these components with upgraded versions. The user may also choose to replace the physiological sensors 204 with other types, such as replacing photodiode sensors with heart rate/blood pressure sensors to measure other types of physiological signals or data. Accordingly, the wearable physiological device 20 is customizable in design and the user can easily disassemble and reassemble the physiological device 20, possibly with repaired/upgraded components.

Physiological Apparatus

Figure 14:
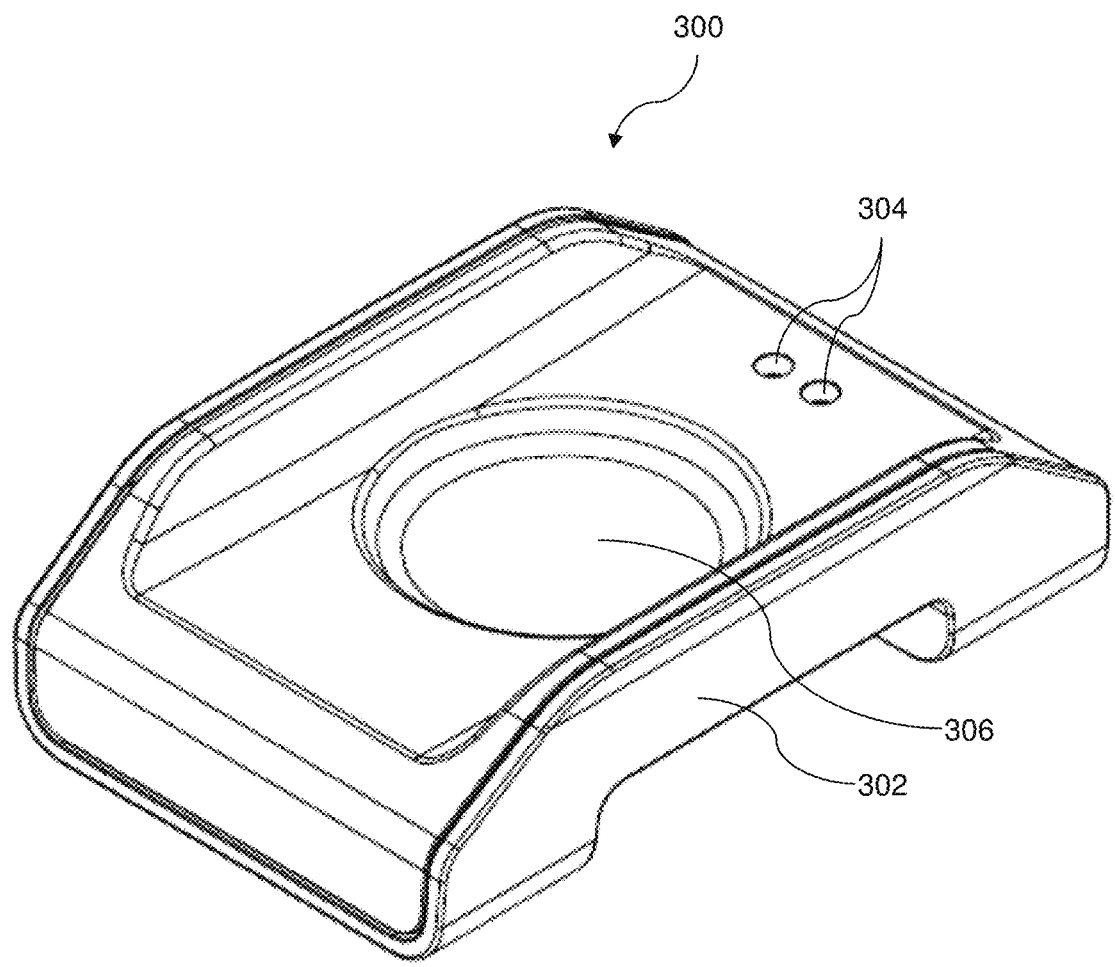
FIG. 14 illustrates a perspective view of a docking station of a physiological apparatus, in accordance with an embodiment of the present disclosure.

In representative or exemplary embodiments of the present disclosure, there is a physiological apparatus including the wearable physiological device 20 and a docking station 300 for docking the physiological device 20 thereto in one orientation, as illustrated in FIG. 14. Specifically, the physiological device 20 is dockable to the docking station 300 for charging of the physiological device 20. When the physiological device 20 is docked at the docking station 300, the physiological apparatus provides another platform or way to review data from the physiological device 20.

The docking station 300 includes a docking assembly 302 and a set of electrical connectors 304 disposed on the docking assembly 302. The docking assembly 302 includes a receptacle portion 306 for receiving the boss portion 206 of the physiological device 20. The boss portion 206 refers to the lower portion of the second housing body 202. The receptacle portion 306 is substantially congruent to the boss portion 206, such that the boss portion 206 is able to fit snugly within the receptacle portion 306 upon docking of the physiological device 20 to the docking station 300. It will be appreciated that the boss portion 206 and receptacle portion 306 have appropriate engineering tolerance to achieve the desired fit.

In some embodiments, upon said docking, the electrical connectors 304 are automatically aligned to the electrical contacts 210 disposed on the boss portion 206. In one embodiment, the boss portion 206 and receptacle portion 306 have a round shape. Various mechanisms, such as a detent, may be implemented to resist or arrest the rotation of the boss portion 206 around the receptacle portion 306. As such, there is only one orientation wherein the receptacle portion 306 can receive the boss portion 206, thereby achieving alignment between the electrical connectors 304 and electrical contacts 210. In another embodiment, the boss portion 206 and receptacle portion 306 have a polygonal shape. Specifically, the polygonal shape is of an irregular polygon, such that there is only one orientation wherein the receptacle portion 306 can receive the boss portion 206.

Figure 15:
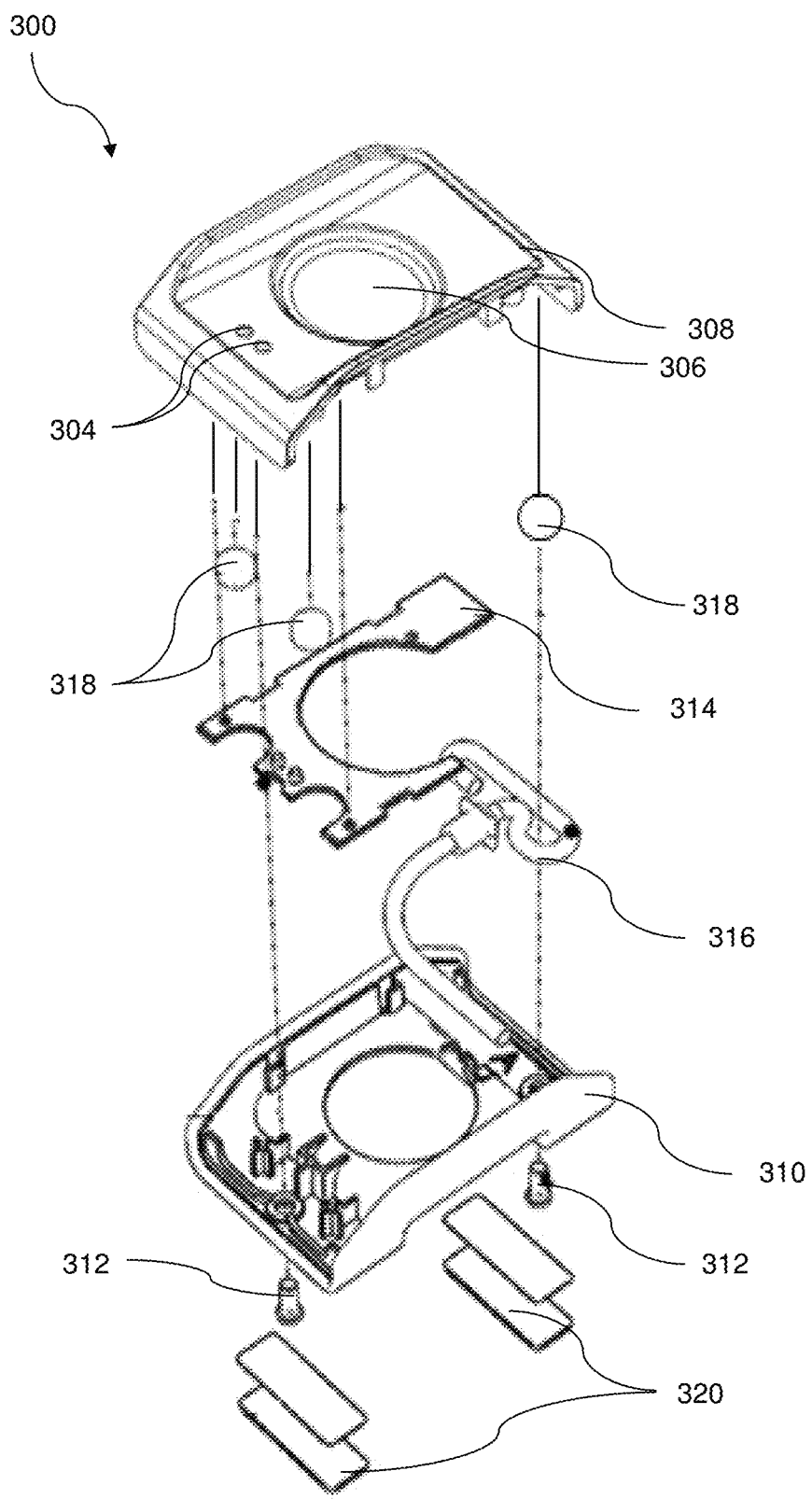
FIG. 15 illustrates an exploded view of the docking station, in accordance with an embodiment of the present disclosure.

Further with reference to FIG. 15, the docking assembly 302 includes a first docking body 308 and a second docking body 310 removably coupled together via a set of fasteners 312. The fasteners 312 may be screws or bolts that can be removed by the user with common household tools such as a screwdriver. Accordingly, the first docking body 308 and second docking body 310 can be easily disassembled and reassembled by the user. Alternatively, each fastener 312 may have snap protrusions attachable to snap receivers disposed on the first docking body 308 and second docking body 310.

The docking station 300 includes a docking circuit assembly 314 removably coupled to the first docking body 308 and/or second docking body 310. The docking circuit assembly 314 includes a PCB. The docking circuit assembly 314 is electrically connected to the electrical connectors 304 and an electrical cable 316 leading to an electrical/communication port. The electrical cable 316 may be a USB cable. The electrical connectors 304 may be in the form of pogo pins. Upon said docking and connection to a power supply, the electrical connectors 304 are connected to the electrical contacts 210, and electricity is conducted from the power supply to the electrical connectors 304 and electrical contacts 210 for charging the battery 212 of the physiological device 20. The user may alternatively connect an external electrical/communication cable between the electrical/communication port and the physiological device 20, such that the physiological device 20 need not remain docked and the user can still use the physiological device 20 during charging.

The docking station 300 includes a set of magnets 318 coupled to the first docking body 308. The magnets 318 are arranged for attracting the boss portion 206 into the receptacle portion 306 and for automatically aligning the electrical connectors 304 to the electrical contacts 210. The boss portion 206, or at least an exterior surface thereof, may be made of a magnetic or metallic material to achieve magnetic attraction with the magnets 318. In addition, the head assembly 30 may include some form of magnetic shielding to protect sensitive components thereof, as will be readily understood by the skilled person.

The docking station 300 includes a set of stands 320 for elevating the docking assembly 302 and for reducing tension in the straps 22 of the physiological device 20 upon said docking. For example, when the physiological device 20 is docked to the docking station 300 with an elevated docking assembly 302, the straps 22 are allowed to dangle in a relaxed state, thereby reducing tension in the straps 22. The stands 320 may be rubberized for stability when the docking station 300 is placed on a surface. The docking station 300 may be made of a lightweight material so that it is portable for use at various places.

Computer Technical Architecture

Figure 16:
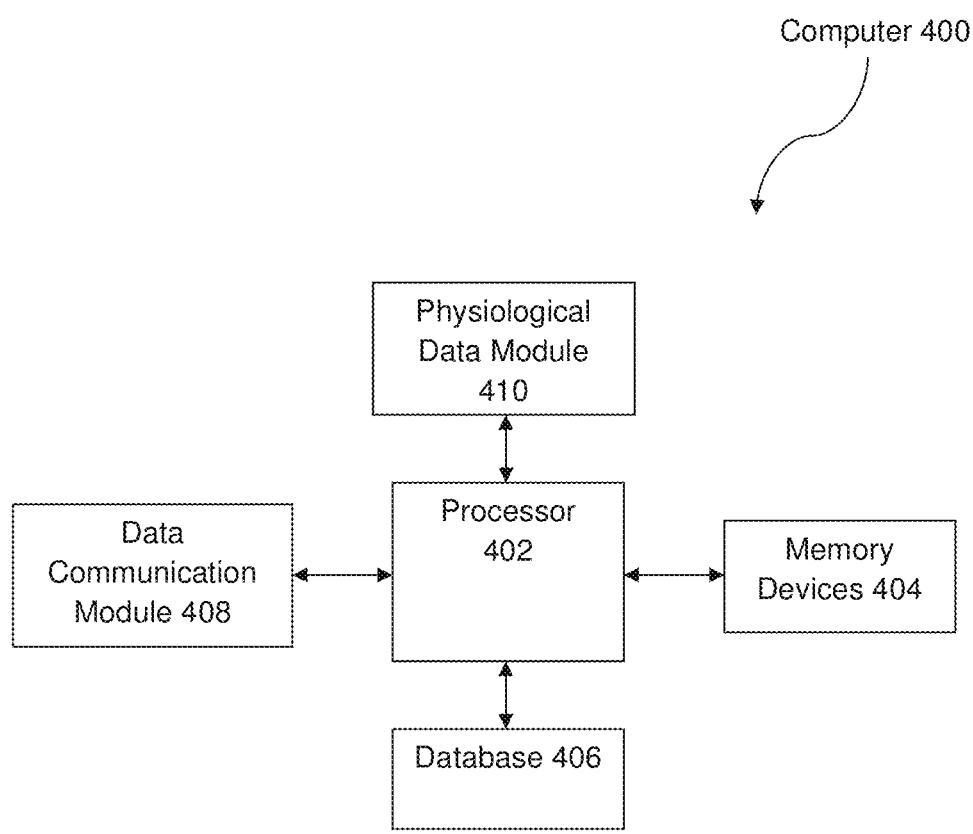
FIG. 16 illustrates a block diagram of the technical architecture of a computer, in accordance with some embodiments of the present disclosure.

FIG. 16 is a block diagram illustrating a technical architecture of a computer 400 in accordance with embodiments of the present disclosure. Some non-limiting examples of the computer 400 are the physiological device 20 and electronic device 50. The computer 400 includes a processor/central processing unit (CPU) 402, memory devices 404, a database 406, a data communication module 408, and a physiological data module 410.

The processor 402 executes instructions, codes, computer programs, and/or scripts which it accesses from the memory devices 404. The processor 402 includes suitable logic, circuitry, and/or interfaces to execute such operations or steps. Some non-limiting examples of the processor 402 include an application-specific integrated circuit (ASIC) processor, a reduced instruction set computing (RISC) processor, a complex instruction set computing (CISC) processor, a field-programmable gate array (FPGA), and the like. While only one processor 402 is shown, multiple processors 402 may be present. Thus, while instructions may be discussed as executed by a processor 402, the instructions may be executed simultaneously, serially, or otherwise executed by one or multiple processors 402 (e.g. in a multi-core configuration).

The memory devices 404 may comprise storage devices (such as flash memory, disk drives, or memory cards), read-only memory (ROM), and random-access memory (RAM). The memory devices 404 store non-transitory instructions operative by the processor 402. The memory devices 404 may be referred to as computer-readable storage media and/or non-transitory computer-readable media. Non-transitory computer-readable media include all computer-readable media, with the sole exception being a transitory propagating signal per se.

The database 406 is any computer-operated hardware suitable for storing data. The database 406 may include multiple storage units such as hard disks and/or solid-state disks in a Redundant Array of Independent Disks (RAID) configuration. The database 406 may include, but is not limited to, a storage area network (SAN) and/or a network attached storage (NAS) system. The data communication module 408 is configured for communication with other computers 400.

The physiological data module 410 is configured to measure and process the physiological data. Various algorithms may be implemented in the physiological data module 410 for performing various assessment and/or diagnosis using the physiological data to generate useful information for the user.

In the foregoing detailed description, embodiments of the present disclosure in relation to a wearable physiological device and a physiological apparatus are described with reference to the provided figures. The description of the various embodiments herein is not intended to call out or be limited only to specific or particular representations of the present disclosure, but merely to illustrate non-limiting examples of the present disclosure. The present disclosure serves to address at least one of the mentioned problems and issues associated with the prior art. Although only some embodiments of the present disclosure are disclosed herein, it will be apparent to a person having ordinary skill in the art in view of this disclosure that a variety of changes and/or modifications can be made to the disclosed embodiments without departing from the scope of the present disclosure. Therefore, the scope of the disclosure as well as the scope of the following claims is not limited to embodiments described herein.

The invention claimed is:

1. A wearable physiological device comprising:
a head assembly comprising a first housing assembly and a second housing assembly removably coupled to each other,
the first housing assembly comprising:
a first housing body;
a first circuit assembly removably coupled to the first housing body; and
a user interface assembly communicatively connected to the first circuit assembly, the second housing assembly comprising:
a second housing body;
a second circuit assembly removably coupled to the second housing body, the second circuit assembly comprising a set of physiological sensors for measuring physiological signals from a user wearing the wearable physiological device;
a removable battery disposed on the second circuit assembly; and a flexible connector communicatively connecting the second circuit assembly to the first circuit assembly, the flexible connector having a first end and a second end, the first end of the flexible connector disposed between the removable battery and the second circuit assembly, the second end of the flexible connector disposed between the removable battery and the first circuit assembly, wherein the physiological signals are communicable from the second circuit assembly to the user interface assembly via the flexible connector.

2. The wearable physiological device according to claim 1, wherein the set of physiological sensors comprises one or more photodiode sensors for measuring photoplethysmogram (PPG) signals from the user.

3. The wearable physiological device according to claim 1, wherein the set of physiological sensors comprises one or more temperature sensors for measuring body temperature of the user.

4. The wearable physiological device according to claim 1, wherein the user interface assembly comprises a display unit.

5. The wearable physiological device according to claim 1, wherein the user interface assembly comprises a set of illumination elements for communicating visual signals to the user.

6. The wearable physiological device according to claim 1, wherein the second housing assembly further comprises a set of electrical contacts disposed on the second housing body, the set of electrical contacts connectable to an electrical supply for charging the battery.

7. The wearable physiological device according to claim 1, wherein the second housing assembly further comprises a sensor protective cover for the set of physiological sensors.

8. The wearable physiological device according to claim 1, further comprising a set of fasteners for removably coupling the first and second housing bodies.

9. The wearable physiological device according to claim 1, further comprising an intermediate support disposed between the first and second housing bodies, the intermediate support surrounding a periphery of the first and second housing bodies, thereby inhibiting liquid ingress into the first and second housing assemblies.

10. The wearable physiological device according to claim 1, further comprising a data communication module communicatively connected to the first circuit assembly.

11. The wearable physiological device according to claim 1, further comprising a set of straps, wherein the first housing assembly further comprises a set of lugs for removably attaching the straps thereto.

12. A physiological apparatus comprising:
(a) a wearable physiological device comprising:
a head assembly comprising a first housing assembly and a second housing assembly removably coupled to each other,
the first housing assembly comprising:
a first housing body;
a first circuit assembly removably coupled to the first housing body; and
a user interface assembly communicatively connected to the first circuit assembly,
the second housing assembly comprising:
a second housing body;
a second circuit assembly removably coupled to the second housing body, the second circuit assembly comprising a set of physiological sensors for measuring physiological signals;
a removable battery disposed on the second circuit assembly;
a flexible connector communicatively connecting the second circuit assembly to the first circuit assembly, the flexible connector having a first end and a second end, the first end of the flexible connector disposed between the removable battery and the second circuit assembly, the second end of the flexible connector disposed between the removable battery and the first circuit assembly; and
a set of electrical contacts disposed on the second housing body,
wherein the physiological signals are communicable from the second circuit assembly to the user interface assembly via the flexible connector; and
(b) a docking station for docking the wearable physiological device thereto in one orientation, the docking station comprising:
(i) a docking assembly; and
(ii) a set of electrical connectors disposed on the docking assembly, the electrical connectors aligned to the electrical contacts of the wearable physiological device upon said docking,
wherein the electrical connectors are connectable to the electrical contacts upon said docking for charging the battery.

13. The physiological apparatus according to claim 12, wherein the second housing body comprises a boss portion and the docking assembly comprises a receptacle portion substantially congruent to the boss portion.

14. The physiological apparatus according to claim 13, wherein the boss portion is receivable into the receptacle portion in only one orientation.

15. The physiological apparatus according to claim 13, wherein upon said docking, the receptacle portion receives the boss portion and the electrical connectors are automatically aligned to the electrical contacts of the wearable physiological device.

16. The physiological apparatus according to claim 15, wherein the docking station further comprises a set of magnets for attracting the boss portion into the receptacle portion and for automatically aligning the electrical connectors to the electrical contacts.

17. The physiological apparatus according to claim 12, wherein the docking station further comprises a communication port for receiving a communication cable.

18. The physiological apparatus according to claim 12, wherein the wearable physiological device further comprises a set of lugs and a set of straps removably attached thereto.

19. The physiological apparatus according to claim 18, wherein the wearable physiological device further comprises a first engagement element disposed at the lugs and each strap comprises a second engagement element matingly engageable with the respective first engagement element.

20. The physiological apparatus according to claim 12, wherein the electrical connectors comprise pogo pins.

* * * * *